US010689448B2

(12) United States Patent
Kim et al.

(10) Patent No.: US 10,689,448 B2
(45) Date of Patent: *Jun. 23, 2020

(54) MONOCLONAL ANTIBODIES TO FIBROBLAST GROWTH FACTOR RECEPTOR 2

(71) Applicant: GALAXY BIOTECH, LLC, Cupertino, CA (US)

(72) Inventors: Kyung Jin Kim, Cupertino, CA (US); Wei-meng Zhao, Palo Alto, CA (US); Hangil Park, San Francisco, CA (US); Maximiliano Vasquez, Palo Alto, CA (US)

(73) Assignee: GALAXY BIOTECH, LLC, Cupertino, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/164,530

(22) Filed: Oct. 18, 2018

(65) Prior Publication Data
US 2019/0153105 A1 May 23, 2019

Related U.S. Application Data

(60) Continuation of application No. 15/674,385, filed on Aug. 10, 2017, now Pat. No. 10,138,301, which is a continuation of application No. 15/172,033, filed on Jun. 2, 2016, now Pat. No. 9,834,609, which is a continuation of application No. 14/071,520, filed on Nov. 4, 2013, now Pat. No. 9,382,324, which is a continuation of application No. 13/284,838, filed on Oct. 28, 2011, now Pat. No. 8,603,987, which is a division of application No. 12/614,282, filed on Nov. 6, 2009, now Pat. No. 8,101,723.

(60) Provisional application No. 61/164,870, filed on Mar. 30, 2009, provisional application No. 61/112,686, filed on Nov. 7, 2008.

(51) Int. Cl.
*C07K 16/28* (2006.01)
*G01N 33/574* (2006.01)
*A61K 39/00* (2006.01)

(52) U.S. Cl.
CPC ... *C07K 16/2863* (2013.01); *G01N 33/57492* (2013.01); *A61K 2039/505* (2013.01); *C07K 2317/24* (2013.01); *C07K 2317/33* (2013.01); *C07K 2317/51* (2013.01); *C07K 2317/565* (2013.01); *C07K 2317/92* (2013.01); *G01N 2333/71* (2013.01)

(58) Field of Classification Search
CPC .......... C07K 16/2863; C07K 2317/565; C07K 2317/51; C07K 2317/33; C07K 2317/24; C07K 2317/92; G01N 33/57492; G01N 2333/71; A61K 2039/505
See application file for complete search history.

(56) References Cited

U.S. PATENT DOCUMENTS

| 5,707,632 | A | 1/1998 | Williams et al. |
|---|---|---|---|
| 5,863,888 | A | 1/1999 | Dionne et al. |
| 6,342,221 | B1 | 1/2002 | Thorpe et al. |
| 7,297,493 | B2 | 11/2007 | Lorenzi et al. |
| 7,872,016 | B2 | 1/2011 | Eswarakumar et al. |
| 8,101,723 | B2 | 1/2012 | Kim et al. |
| 8,603,987 | B2 | 12/2013 | Kim et al. |
| 9,382,324 | B2 | 7/2016 | Kim et al. |
| 9,834,609 | B2 | 12/2017 | Kim et al. |
| 10,138,301 | B2 | 11/2018 | Kim et al. |
| 2005/0147612 | A1 | 7/2005 | Yayon et al. |
| 2007/0248605 | A1 | 10/2007 | Hestir et al. |
| 2009/0170715 | A1 | 7/2009 | Glinsky |
| 2009/0311250 | A1 | 12/2009 | Chant et al. |
| 2010/0111944 | A1 | 5/2010 | Pollock et al. |
| 2011/0091473 | A1 | 4/2011 | Golab et al. |

FOREIGN PATENT DOCUMENTS

| KR | 1020040020107 | 3/2004 |
|---|---|---|
| WO | WO 2001/079266 A1 | 10/2001 |
| WO | WO 2003/063893 A2 | 8/2003 |
| WO | WO 2005/066211 A2 | 7/2005 |
| WO | WO 2007/144893 A2 | 12/2007 |
| WO | WO 2008/042236 A2 | 4/2008 |
| WO | WO 2008/052796 A1 | 5/2008 |
| WO | WO 2009/100105 A2 | 8/2009 |
| WO | WO 2010/040571 A2 | 4/2010 |
| WO | WO 2010/054265 A2 | 5/2010 |
| WO | WO 2011/025814 A1 | 3/2011 |

OTHER PUBLICATIONS

Adelaide et al., "Integrated Profiling of Basal and Luminal Breast Cancers," *Cancer Res.*, 67:11565-11575, (2007).
Bai et al., "GP369, an FGFR2-IIIb-specific antibody, exhibits potent antitumor activity against human cancers driven by activated FGFR2 signaling," *Cancer Res.*, 70:7630-7639, (2010).
Beer et al., "Expression and Function of Keratinocyte Growth Factor and Activin in Skin Morphogenesis and Cutaneous Wound Repair," *Journal of Investigative Dermatology Symposium Proceedings*, 5:34-39 (2000).
Beer et al., "Fibroblast Growth Factor (FGF) Receptor 1-IIIb is a Naturally Occurring Functional Receptor for FGFs that is Preferentially Expressed in the Skin and the Brain," *J Biol Chem*, 275:16091-16097 (2000).
Byron et al., "Inhibition of Activated Fibroblast Growth Factor Receptor 2 in Endometrial Cancer Cells Induces Cell Death Despite PTEN Abrogation," *Cancer Res.*, 68:6902-6907, (2008).
Campbell, "General properties and applications of monoclonal antibodies," Monoclonal Antibody Technology, pp. 1-32, (1984).
Carter et al., "Identification and validation of cell surface antigens for antibody targeting in oncology," *Endocrine-Related Cancer*, 11:659-687, (2004).

(Continued)

*Primary Examiner* — Ruixiang Li
(74) *Attorney, Agent, or Firm* — Alston & Bird LLP

(57) ABSTRACT

The present invention is directed toward a monoclonal antibody to fibroblast growth factor receptor 2, a pharmaceutical composition comprising same, and methods of treatment comprising administering such a pharmaceutical composition to a patient.

18 Claims, 17 Drawing Sheets

Specification includes a Sequence Listing.

(56) References Cited

OTHER PUBLICATIONS

Casset et al., "A peptide mimetic of an anti-CD4 monoclonal antibody by rational design," Biochemical and Biophysical Research Communications, 307: 198-205, (2003).
Chen et al., "Selection and analysis of an optimized anti-VEGF antibody: crystal structure of an affinity matured Fab in complex with antigen," Journal of Molecular Biology, 293:865-881, (1999).
Cho et al., "Enhanced Expression of Keratinocyte Growth Factor and its Receptor Correlates with Venous Invasion in Pancreatic Cancer," Am. J. Pathol., 170(6):1964-1974, doi: http://dx.doi.org/10.2353/ajpath.2007.060935, (2007).
Davies et al., "Affinity improvement of single antibody VH domains: residues in all three hypervariable regions affect antigen binding," Immunotechnology, 2(3):169-179, (1996).
Davies et al., "Somatic Mutations of the Protein Kinase Gene Family in Human Lung Cancer," Cancer Res., 65:7591-7595, (2005).
De Moerlooze et al., "An important role for the IIIb isoform of fibroblast growth factor receptor 2 (FGFR2) in mesenchymal-epithelial signalling during mouse organogenesis," Development, 127:483-492, (2000).
De Pascalis et al., "Grafting of abbreviated complementarity determining regions containing specificity determining residues essential for ligand contact to engineer a less immunogenic humanized monoclonal antibody," Journal of Immunology, 169: 3076-3084, (2002).
Dutt et al., "Drug-sensitive FGFR2 mutations in endometrial carcinoma," Proc Natl Acad Sci USA, 105:8713-7, (2008).
Easton et al., "Genome-wide Association Study Identifies Novel Breast Cancer Susceptibility Locus," Nature, 447:1087-1093, (2007).
Finch and Rubin, "Keratinocyte Growth Factor Expression and Activity in Cancer: Implications for Use in Patients with Solid Tumors," Journal of the National Cancer Institute, 98:812-824 (2006).
Fortin et al., "Distinct fibroblast growth factor (FGF)/FGF receptor signaling pairs initiate diverse cellular responses in the oligodendrocyte lineage," J Neurosci, 25:7470-4709, (2005).
GenBank: Accession No. AAF26719.1, "Fibroblast growth factor-10: a stromal mediator of epithelial function in the ovine uterus," Nov. 17, 2000.
GenBank: Accession No. AB181225.1, "Ovine endometrral expression of fibroblast growth factor (FGF) 2 and conceptus expression of FGF receptors during early pregnancy," Mar. 5, 2008.
Grose et al., "Fibroblast growth factor signaling in tumorigenesis," Cytokine Growth Factor Rev, 16:179-86, (2005).
Grose et al., "The Role of Fibroblast Growth Factor Receptor 2b in Skin Homeostasis and Cancer Development," The Embo Journal, 26:1268-1278 (2007).
Hattori et al., "Immunohistochemical detection of K-sam protein in stomach cancer," Clin Cancer Res, 2:1373-81, (1996).
Holt et al., "Domain antibodies: proteins for therapy", Trends in Biotechnology, 21(11):484-490, (2003).
Hughes, "Differential Expression of the Fibroblast Growth Factor Receptor (FGFR) Multigene Family in Normal Human Adult Tissues," J Histochem Cytochem, 45:1005-1019 (1997).
Hunter et al., "A Genome-Wide Association Study Identifies Alleles in FGFR2 Associated With Risk of Sporadic Postmenopausal Breast Cancer," Nature Genetics, 39:870-874, (2007).
Ibrahimi et al., "Biochemical Analysis of Pathogenic Ligand-Dependent FGFR2 Mutations Suggests Distinct Pathophysiological Mechanisms for Craniofacial and Limb Abnormalities," Human Molecular Genetics, 13:2313-2324, (2004).
Itoh et al., "Preferential Alternative Splicing in Cancer Generates a K-sam Messenger RNA with Higher Transforming Activity," Cancer Res., 54:3237-3241, (1994).
Jang et al., "Mutations in Fibroblast Growth Factor Receptor 2 and Fibroblast Growth Factor Receptor 3 Genes Associated with Human Gastric and Colorectal Cancers," Cancer Res., 61:3541-3543, (2001).
Katoh "Cancer genomics and genetics of FGFR2 (Review)," Int J Oncology, 33:233-237, (2008).
Kono et al., "Impaired Antibody-Dependent Cellular Cytotoxicity Mediated by Herceptin in Patients with Gastric Cancer," Cancer Res 62:5813-5817, (2002).
Kunii et al., "FGFR2-amplified gastric cancer cell lines require FGFR2 and Erbb3 signaling for growth and survival," Cancer Res, 68:2340-2348, (2008).
Kurban, et al., "Expression of keratinocyte growth factor receptor (KGFR/FGFR2 nib) in human uterine cervical cancer," Oncology Reports, 11:987-991, (2004).
Liang et al., "Genetic Variants in Fibroblast Growth Factor Receptor 2 (FGFR2) Contribute to Susceptibility of Breast Cancer in Chinese Women," Carcinogenesis, 29: 2341-2346, (2008).
Luqmani et al., "Expression of Basic Fibroblast Growth Factor, FGFR1 and FGFR2 in Normal and Malignant Human Breast, and Comparison with Other Normal Tissues," Br. J. Cancer, 66:273-280, (1992).
Mac Callum et al., "Antibody-antigen interactions: contact analysis and binding site topography," Journal of Molecular Biology, 262: 732-745, (1996).
Masayuki et al., "AZD2171 Shows Potent Antitumor Activity Against Gastric Cancer Over-Expressing Fibroblast Growth Factor Receptor 2/Keratinocyte Growth Factor Receptor," Clinical Cancer Research, 13(10):3051-3057, (2007).
Matsunobu et al., "Expression of Keratinocyte Growth Factor Receptor Correlates with Expansive Growth and Early Stage of Gastric Cancer," International Journal of Oncology, 28:307-314, (2006).
McKay et al., "Tolerance to single, but not multiple, amino acid replacements in antibody V—H CDR2: A means of minimizing B cell wastage from somatic hypermutation?," Journal of Immunology, 156(9):3285-3291, (1996).
Miki, et al., "Determination of ligand-binding specificity by alternative splicing: Two distinct growth factor receptors encoded by a single gene," Proc. Natl. Acad. Sci. USA, Biochemistry, 89:246-250, (1992).
Mohammadi et al., "Structural basis for fibroblast growth factor receptor activation," Cytokine Growth Factor Rev, 16:107-137, (2005).
Moloney et al., "Exclusive Paternal Origin of New Mutations in Apert Syndrome," Nature Genetics, 13:48-53, (1996).
Mor et al., "DNA Amplification in Human Gastric Carcinomas," Cancer Genet Cytogenet, 65:111-114, (1993).
Mor et al., "Novel DNA Sequences at Chromosome 10Q26 are Amplified in Human Gastric Carcinoma Cell Lines: Molecular Cloning by Competitive DNA Reassociation," Nucleic Acids Research, 19:117-123, (1991).
Nakamura et al., "A novel molecular targeting compound as K-samII/FGF-R2 phosphorylation inhibitor, Ki23057, for scirrhous gastric cancer," Gastroenterology, 131:1530-1541, (2006).
Nakatani et al., "Isolation of an Amplified DNA Sequence in Stomach Cancer," Jpn J. Cancer Res., 81:707-710, (1990).
Ogle et al., "Regulation of Cranial Suture Morphogenesis," Cells Tissues Organs, 176:54-60, (2004).
Ornitz et al., "Fibroblast growth factors," Genome Biol, 2:REVIEWS3005, (2001).
Ornitz et al., "Receptor specificity of the fibroblast growth factor family," J Biol Chem, 271:15292-15297, (1996).
Otte, et al., "Expression of keratinocyte growth factor and its receptor in colorectal cancer," European Journal of Clinical Investigation, 30:222-229, (2000).
Pascal et al., "Correlation of mRNA and protein levels: Cell type-specific gene expression of cluster designation antigens in the prostate," BMC Genomics, 9:246, 13 pages, (2008).
PCT/US2009/063647 International Preliminary Report on Patentability and Written Opinion dated May 10, 2011.
PCT/US2009/063647 International Search Report dated Jun. 23, 2010.
Pollock et al., "Frequent activating FGFR2 mutations in endometrial carcinomas parallel germline mutations associated with craniosynostosis and skeletal dysplasia syndromes," Oncogene, 26:7158-7162, (2007).

(56) References Cited

OTHER PUBLICATIONS

Presta et al., "Fibroblast growth factor/fibroblast growth factor receptor system in angiogenesis," Cytokine Growth Factor Rev, 16:159-178, (2005).
R&D Systems online catalog page for MAB665 dated Nov. 15, 2010.
R&D Systems online catalog page for MAB665 dated Mar. 1, 2005.
Rudikoff et al., "Single amino acid substitution altering antigen-binding specificity," Proceedings of the National Academy of Sciences, 79:1979-1983, (1982).
Steele et al., "Induction of FGF receptor 2-IIIb expression and response to its ligands in epithelial ovarian cancer," Oncogene, 20:5878-5887, (2001).
Supplementary European Search Report and European Search Opinion for application EP09825523.5 dated May 7, 2012.
Supplementary European Search Report and European Search Opinion for application EP14188785.1 dated Feb. 2, 2015.
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, 13(10):3051-3067, (2007).
Tamaru et al., "Estrogen receptor-associated expression of keratinocyte growth factor and its possible role in the inhibition of apoptosis in human breast cancer," Lab. Invest, 84(11):1460-1471, (2004).
Tannheimer et al., "Characterization of Fibroblast Growth Factor Receptor 2 Overexpression in the Human Breast Cancer Cell Line SUM-52 PE," *Breast Cancer Res*, 2:311-320 (2000).
Trudel et al., "The inhibitory anti-FGFR3 antibody, PRO-001, is cytotoxic to t(4;14) multiple myeloma cells," Blood, 107:4039-4046, (2006).
Tsujimoto et al., "Amplification of Growth Factor Receptor Genes and DNA Ploidy Pattern in the Progression of Gastric Cancer," *Virchows Arch*, 431:383-389, (1997).
U.S. Appl. No. 12/614,282, Non-Final Rejection dated Apr. 7, 2011.
U.S. Appl. No. 12/614,282, Notice of Allowance dated Sep. 29, 2011.
U.S. Appl. No. 12/614,282, Requirement for Restriction/Election dated Dec. 27, 2010.
U.S. Appl. No. 13/284,838, Non-Final Rejection dated Jul. 29, 2013.
U.S. Appl. No. 13/284,838, Notice of Allowance dated Oct. 4, 2013.
U.S. Appl. No. 13/284,838, Requirement for Restriction/Election dated Feb. 1, 2013.
U.S. Appl. No. 14/071,520, Final Rejection mailed 13/30/2015.
U.S. Appl. No. 14/071,520, Non-Final Rejection dated Jul. 14, 2015.
U.S. Appl. No. 14/071,520, Notice of Allowance dated Mar. 31, 2016.
U.S. Appl. No. 14/071,520, Requirement for Restriction/Election dated Mar. 23, 2015.
Ueda et al., "Deletion of the Carboxyl-Terminal Exons of K-sam/FGFR2 by Short Homology-Mediated Recombination, Generating Preferential Expression of Specific Messenger RNAs," *Cancer Res.*, 59:6080-6086, (1999).
Vajdos et al., "Comprehensive functional maps of the antigen-binding site of an anti-ErbB2 antibody obtained with shotgun scanning mutagenesis," J. Mol. Biol., 320:415-428, (2002).
Visco et al., "Expression of keratinocyte growth factor receptor compared with that of epidermal growth factor receptor and erbB-2 in endometrial adenocarcinoma," Int. J. Oncol., 15(3):431-435, doi: https://doi.org/10.3892/ijo.15.3.431, (1999).
Watanabe, et al., "Overexpression of keratinocyte growth factor in cancer cells and enterochromaffin cells in human colorectal cancer," *Pathology International*, 50:363-372, (2000).
Wei, et al. "Generation and characterization of monoclonal antibodies to human keratinocyte growth factor receptor," Hybridoma, 25(3):115-124, (2006).
Werner, "Molecular and Cellular Mechanisms of Tissue Repair", *Experimental Dermatology*, 14(10):786-787, (2005).
Winter, et al., "Humanized antibodies," *Immunology Today*, 14(6):243-246, (1993).
Wu et al., "Humanization of a murine monoclonal antibody by simultaneous optimization of framework and CDR residues," Journal of Molecular Biology, 294: 151-162, (1999).
Yashiro et al., "Establishment of two new scirrhous gastric cancer cell lines: analysis of factors associated with disseminated metastasis," Br J Cancer, 72:1200-1210 (1995).
Yoshinoi, et al., "Keratinocyte growth factor receptor expression in normal colorectal epithelial cells and differentiated type of colorectal cancer," *Oncology Reports*, 13:247-252, (2005).
Zhang et al., "Receptor specificity of the fibroblast growth factor family. The complete mammalian FGF family," J Biol Chem, 281:15694-156700, (2006).
Zhao et al., "Another Approach: Anti-FGFR2 MABs," *Proc. Am. Assoc. Cancer Res.*, Denver, CO, Poster Presentation No. 1236, Apr. 18-22, 2009.
Zhao et al., "Monoclonal antibodies to fibroblast growth factor receptor 2 effectively inhibit growth of gastric tumor xenografts," Clin Cancer Res, 16:5750-5758, (2010).
U.S. Appl. No. 15/172,033 Non-Final Office Action dated Sep. 29, 2016.
U.S. Appl. No. 15/172,033 Notice of Allowance dated Mar. 13, 2017.
EP 1719118.3 Extended European Search Report dated Jan. 23, 2018.
U.S. Appl. No. 15/674,385, Non-Final Office Action dated Jan. 16, 2018.
U.S. Appl. No. 15/674,385, Notice of Allowance dated Jul. 19, 2018.

| | Isotype | Epitope | Blocking ELISA FGFR2IIIb-Fc binding to | | | FACS SNU-16 | | 293 transfectant | In vivo Anti-tumor |
| | | | Flag-FGF1 | Flag-FGF2 | | Live | Fixed | S252W | SNU-16 |
|---|---|---|---|---|---|---|---|---|---|
| GAL-FR21 | IgG₁ | D3 | + | +++ | | +++ | +++ | +++ | ++++ |
| GAL-FR22 | IgG₂ᵦ | D2-D3 | - | ++ | | +++ | - | +++ | +++ |
| GAL-FR23 | IgG₂ᵦ | D1 | - | - | | +++ | + | +++ | +++ |

FIGURE 2

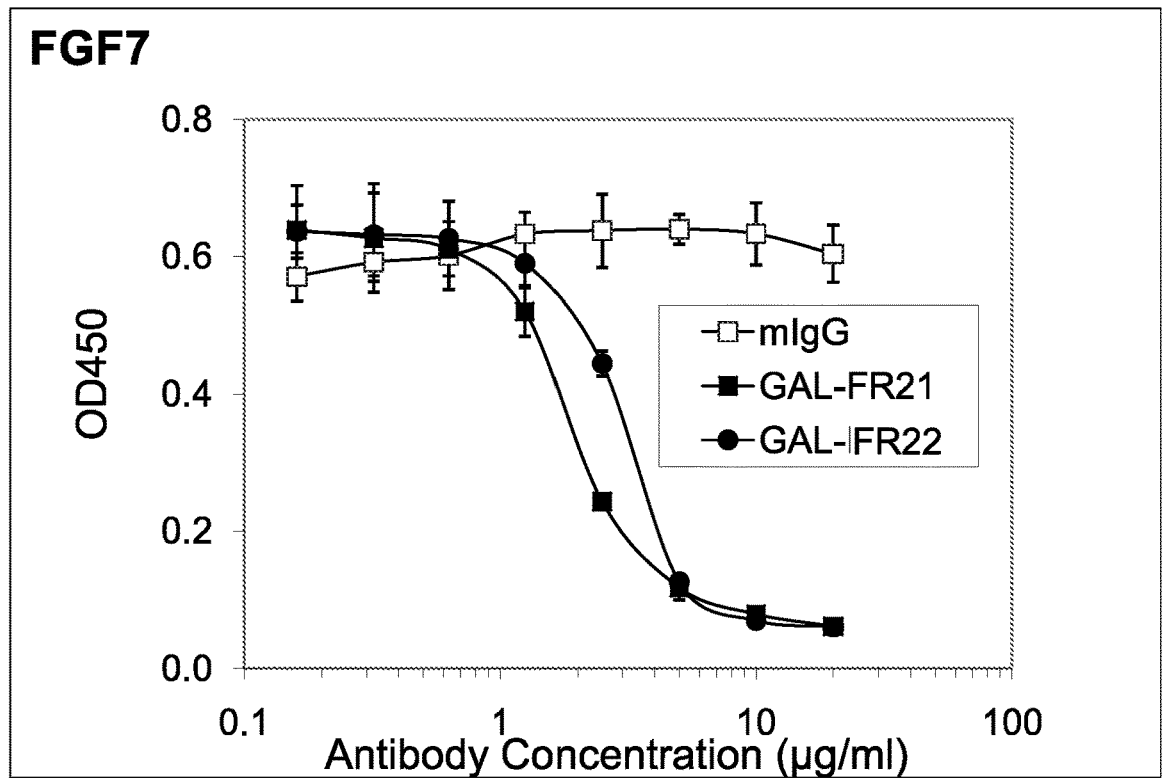
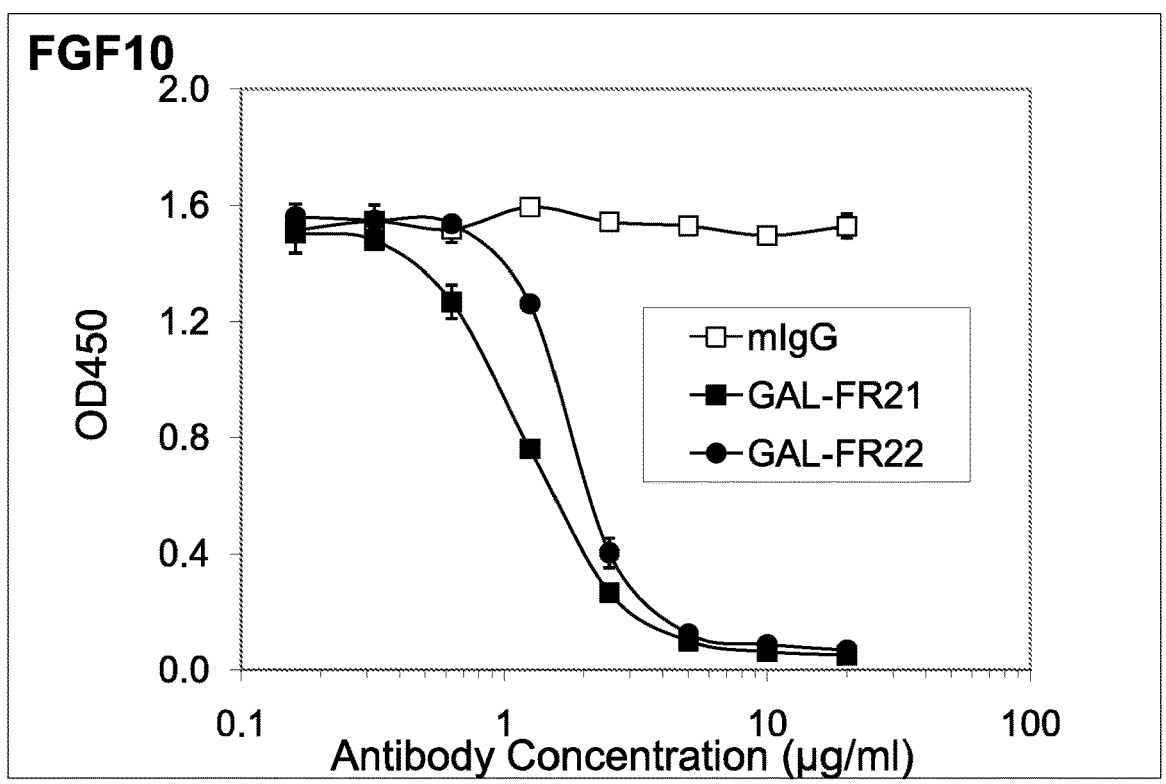
FIGURE 8B

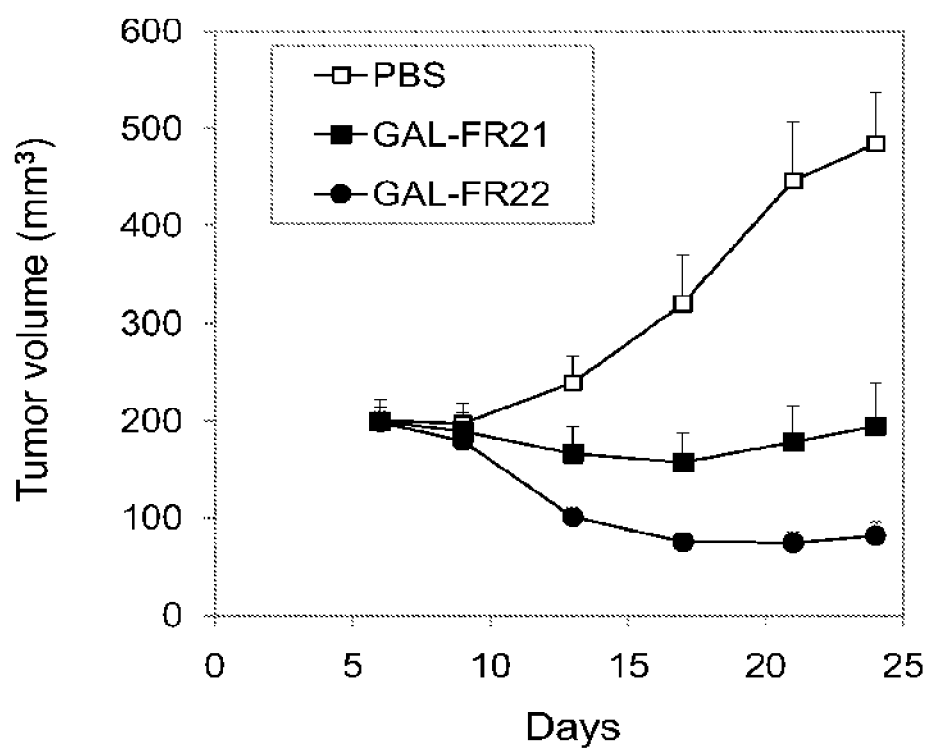
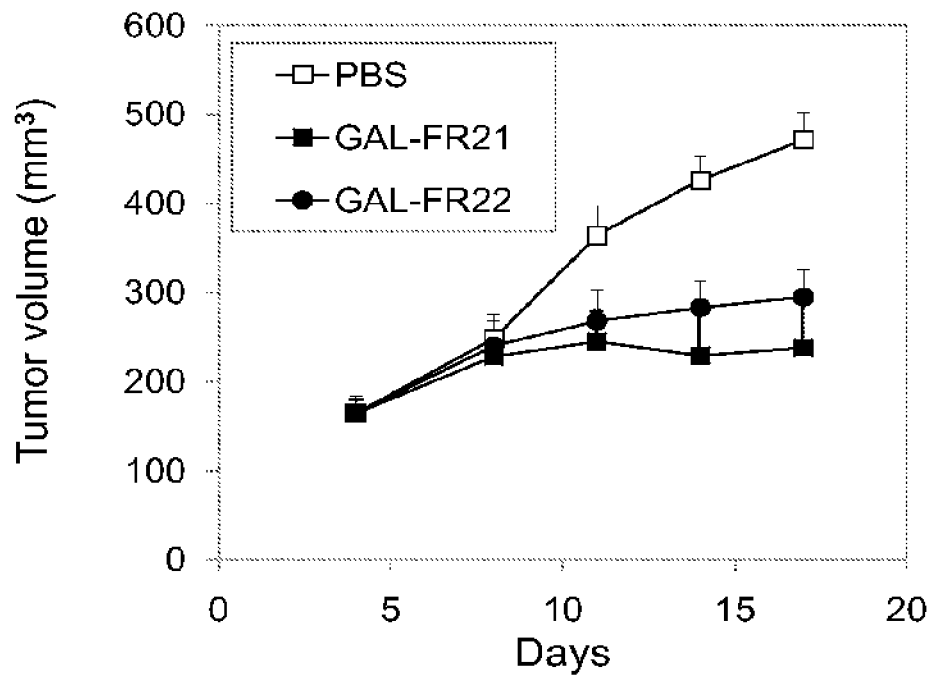
FIGURE 10

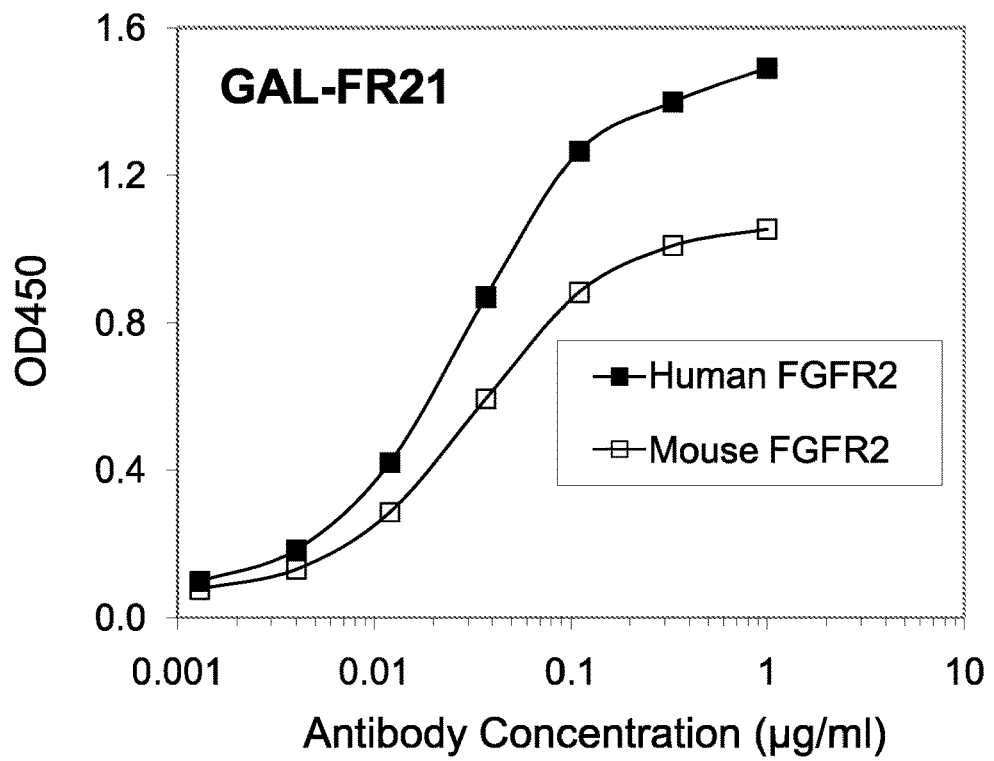
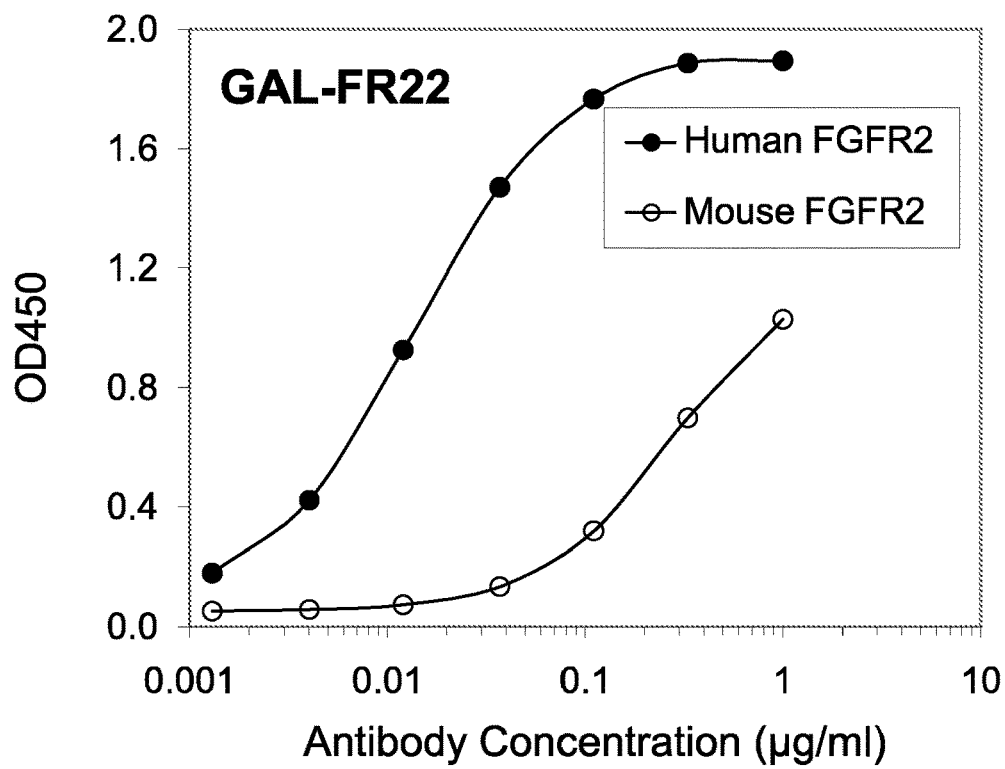
FIGURE 11

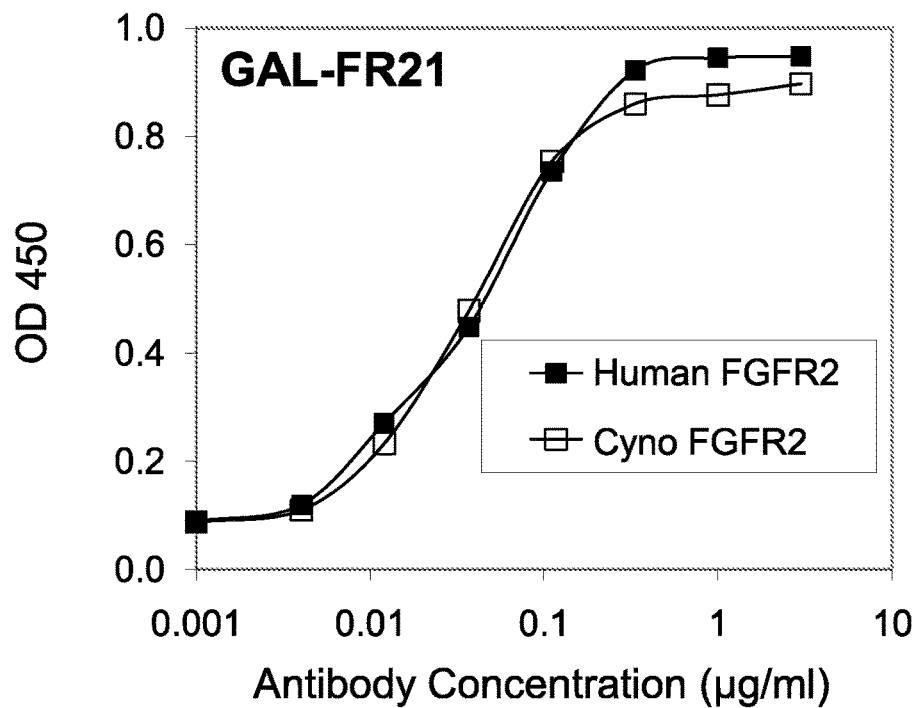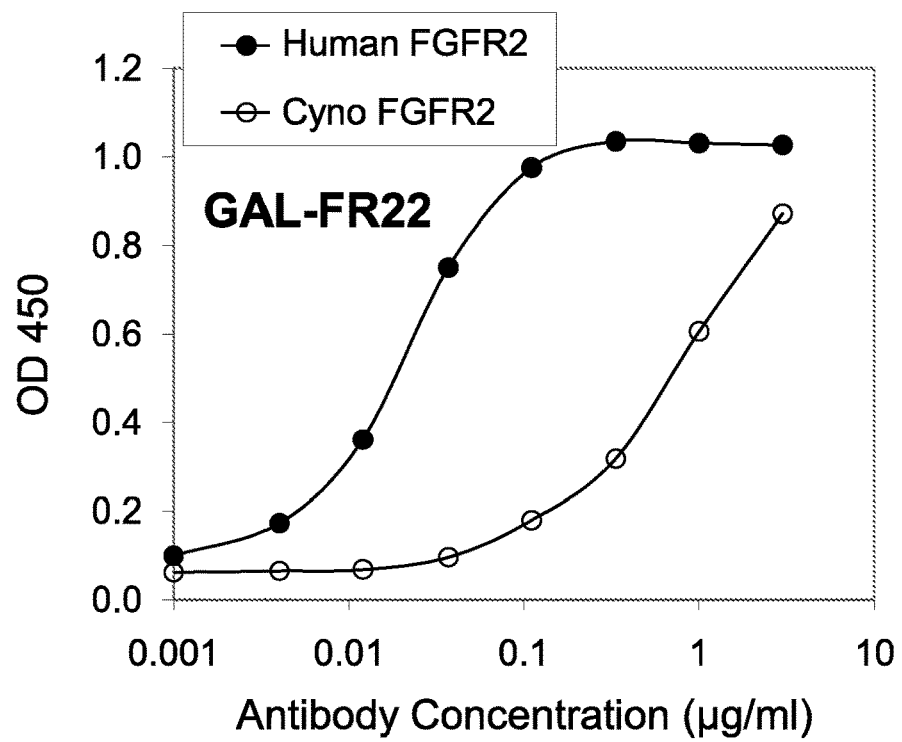
FIGURE 12

A

```
                        1           2           3           4
               1234567890  1234567890  1234567890  1234567890
GAL-FR21       NIVMTQSPKS  MSMSVGDRVS  ITCKASQGVS  NDVAWYQKKP
HuGAL-FR21     DIQMTQSPSS  LSASVGDRVT  ITCKASQGVS  NDVAWYQQKP
CAG27369       DIQMTQSPSS  LSASVGDRVT  ITCqasqdis  nylnWYQQKP 5           6           7           8
               1234567890  1234567890  1234567890  1234567890
GAL-FR21       GQSPKLLIYS  ASYRYTGVPD  RFTGSGSGTD  FTFTISNVQA
HuGAL-FR21     GKAPKLLIYS  ASYRYTGVPS  RFSGSGSGTD  FTFTISSLQP
CAG27369       GKAPKLLIYd  asnletGVPS  RFSGSGSGTD  FTFTISSLQP 9          10
               1234567890  1234567890  1234567
GAL-FR21       EDLAVYYCQQ  HSTTPYTFGG  GTKLEIK
HuGAL-FR21     EDIATYYCQQ  HSTTPYTFGQ  GTKLEIK
CAG27369       EDIATYYCqq  ydnlpptFGQ  GTKLEIK
```

B

```
                         1           2           3           4
                1234567890  1234567890  1234567890  1234567890
GAL-FR21        QVQLQQPGAE  VVKPGASVKM  SCKASGYIFT  TYNVHWVKQT
HuGAL-FR21      QVQLVQSGAE  VKKPGSSVKV  SCKASGYIFT  TYNVHWVRQA
AAB00780        QVQLVQSGAE  VKKPGSSVKV  SCKASGGTFS  syaisWVRQA 5      a    6           7           8
                1234567890  12234567890  1234567890  1234567890
GAL-FR21        PGQGLEWIGS  IYPDNGDTSYN  QNFKGKATLT  ADKSSSTAYI
HuGAL-FR21      PGQGLEWIGS  IYPDNGDTSYN  QNFKGRATIT  ADKSTSTAYM
AAB00780        PGQGLEWMGg  iipifgtanya  qkfqgRVTIT  ADKSTSTAYM abc           9          10          11
                1222234567890  1234567890  1234567890  123
GAL-FR21        QLSSLTSEDSAVY  YCARGDF     AYWGQGTLVT  VSV
HuGAL-FR21      ELSSLRSEDTAVY  YCARGDF     AYWGQGTLVT  VSS
AAB00780        ELSSLRSEDTAVY  YCARgstvttgdf dYWGQGTLVT VSS
```

```
                            1          2          3          4
                   1234567890 1234567890 1234567890 1234567890
GAL-FR22           DIQMTQSPSS LSASLGGRVT ITCKASQDIK NYIAWYQHKP 5          6          7          8
                   1234567890 1234567890 1234567890 1234567890
GAL-FR22           GKSPRLLIHY TSTLQPGVPS RFSGSGSGRD YSFSISNLEP 9         10
                   1234567890 1234567890 1234567
GAL-FR22           EDIATYYCLQ YDDLYM_FGG GTKLDIK
```

B

```
                            1          2          3          4
                   1234567890 1234567890 1234567890 1234567890
GAL-FR22           QVQLKQSGPG LVQPSQSLSI TCTVSGFSLT SFGVHWVRQS 5          6          7          8
                   1234567890 1234567890 1234567890 1234567890
GAL-FR22           PGKGLEWLGV IWSGGSTDYN ADFRSRLSIS KDNSKSQIFF abc           9       10abcd         11
                   1222234567890 1234567890000C0 1234567890 123
GAL-FR22           KMNSLQPDDTAIY YCANFYYGYDDYVM DYWGQGTSVT VSS
```

FIGURE 16

MONOCLONAL ANTIBODIES TO FIBROBLAST GROWTH FACTOR RECEPTOR 2

CROSS-REFERENCE TO RELATED APPLICATIONS

This application is a continuation of U.S. patent application Ser. No. 15/674,385 filed Aug. 10, 2017, which is a continuation of U.S. patent application Ser. No. 15/172,033 filed Jun. 2, 2016 now U.S. Pat. No. 9,834,609, which is a continuation of U.S. patent application Ser. No. 14/071,520 filed Nov. 4, 2013 now U.S. Pat. No. 9,382,324, which is a continuation of U.S. patent application Ser. No. 13/284,838 filed Oct. 28, 2011 now U.S. Pat. No. 8,603,987, which is a divisional of U.S. patent application Ser. No. 12/614,282 filed Nov. 6, 2009 now U.S. Pat. No. 8,101,723, which claims the benefit under 35 USC 119(e) of U.S. Patent Application No. 61/164,870 filed Mar. 30, 2009 and U.S. Patent Application No. 61/112,686 filed Nov. 7, 2008, each of which is incorporated by reference in its entirety for all purposes.

STATEMENT OF GOVERNMENT INTEREST

The invention described in this application was made in part with funds provided by Grant 5R44 CA101283-03 from the National Institutes of Health. The US Government has certain rights in this invention.

REFERENCE TO A SEQUENCE LISTING

This application includes an electronic sequence listing in a file named "SEQTXT 022382-000920US522386 SEQL-ST.TXT", created Oct. 18, 2018, and containing 14,623 bytes, which is hereby incorporated by reference in its entirety for all purposes.

FIELD OF THE INVENTION

The present invention relates generally to the combination of monoclonal antibody (mAb) and recombinant DNA technologies for developing novel biologics, and more particularly, for example, to the production of monoclonal antibodies that bind to and neutralize Fibroblast Growth Factor Receptor 2.

BACKGROUND OF THE INVENTION

There are 22 known members of the Fibroblast Growth Factor (FGF) family, ranging in size from 17 to 34 kDa and sharing an internal core region of similarity, which can be grouped into 7 subfamilies based on their similarity in activity and sequence (Ornitz et al., Genome Biol. 2:3005.1, 2001). For example, the FGF1 subgroup consists of the prototypical FGFs, FGF1 (acidic FGF) and FGF2 (basic FGF); the FGF4 subgroup consists of FGF4, FGF5 and FGF6; and the FGF7 subfamily consists of FGF3, FGF7, FGF10 and FGF22 (Zhang et al., J. Biol. Chem. 281:15694, 2006).

One form of FGF2 is an 18 kDa non-glycosylated polypeptide consisting of 146 amino acids derived from a 155 aa precursor (Ornitz et al., Genome Biol. 2:3005.1, 2001; Okada-Ban et al., Int. J. Biochem. Cell. Biol. 32:263, 2000). An exemplary sequence for a human 146 amino acid FGF2 is provided in SEQ ID NO:4 of US20020115603. Unlike most other FGFs, FGF2 does not encode a signal sequence for secretion, but the 18 kDa form can be secreted by an unconventional energy-dependent pathway independent of the ER-Golgi complex. The other FGF1 subfamily member, FGF1 itself, has size and structure similar to FGF2 and also lacks a signal sequence but can be secreted. Another FGF of interest here is FGF7, also called keratinocyte growth factor (KGF), which is produced by cells of mesenchymal origin and stimulates epithelial cell proliferation (Finch et al., Adv. Cancer Res. 91:69, 2004; Finch et al., J. Natl. Cancer Inst. 98:812, 2006). KGF is expressed in a number of organs including lung, prostate, mammary, digestive tract and skin and is implicated in organ development and repair of cutaneous wounds (Cho et al., Am. J. Pathol. 170:1964, 2007).

The FGF family members bind to only four known tyrosine kinase receptors, Fibroblast Growth Factor Receptors 1-4 (FGFR1-4) and their isoforms, with the various FGFs binding the different FGFRs to varying extents (Zhang et al., J. Biol. Chem. 281:15694, 2006). A protein sequence of human FGFR2 is provided in, e.g., GenBank Locus AF487553. Each FGFR consists of an extracellular domain (ECD) comprising three immunoglobulin (Ig)-like domains (D1, D2 and D3), a single transmembrane helix, and an intracellular catalytic kinase domain (Mohammadi et al., Cytokine Growth Factor Revs, 16:107, 2005) as illustrated in FIG. 1. There is a contiguous stretch of acidic amino acids in the linker between D1 and D2 called the "acid box" (AB). The region containing D1 and AB is believed to be involved in autoinhibition of the receptor, which is relieved by binding to ligand. The FGFRs are characterized by multiple alternative splicing of their mRNAs, leading to a variety of isoforms (Ornitz et al., J. Biol. Chem. 271:15292, 1996; see also Swiss-Prot P21802 and isoforms P21802-1 to -20 for sequences of FGFR2 and its isoforms). Notably, there are forms containing all three Ig domains (α isoform) or only the two Ig domains D2 and D3 domains without D1 (β isoform). Of particular importance in FGFR1-FGFR3, while all forms contain the first half of D3 denoted IIIa, two alternative exons can be utilized for the second half of D3, leading to IIIb and IIIc forms. For FGFR2, these are respectively denoted FGFR2IIIb and FGFR2IIIc (or just FGFR2b and FGFR2c); the corresponding beta forms are denoted FGFR2(beta)IIIb and FGFR2(beta)IIIc. The FGFR2IIIb form of FGFR2 (also denoted K-sam-II) is a high affinity receptor for both FGF1 and KGF whereas FGFR2IIIc (also denoted K-sam-1) binds both FGF1 and FGF2 well but does not bind KGF (Miki et al., Proc. Natl. Acad. Sci. USA 89:246, 1992). Indeed, FGFR2IIIb is the only receptor for KGF (Ornitz et al., 1996, op. cit.) and is therefore also designated KGFR.

The FGFRs and their isoforms are differentially expressed in various tissues. Notably, FGFR2IIIb (and the IIIb forms of FGFR1 and FGFR3) are expressed in epithelial tissues, while FGFRIIIc is expressed in mesenchymal tissues (Duan et al., J. Biol. Chem. 267:16076, 1992; Ornitz et al., 1996, op. cit.). Certain of the FGF ligands of these receptors have an opposite pattern of expression. Thus, FGF3 subfamily members including FGF7 (KGF) bind only to FGFRIIIb (Zhang et al., op. cit.) and are expressed in mesenchymal tissues so may be paracrine effectors of epithelial cells (Ornitz et al., 1996, op. cit.). In contrast, the FGF4 subfamily members FGF4-6 bind to FGFR2IIIc and are expressed in both epithelial and mesenchymal lineages so may have either autocrine or paracrine functions. Because of the expression patterns of the isoforms of FGFR2 and their ligands, FGFR2 plays a role in epithelial-mesynchymal interactions (Finch et al., Dev. Dyn. 203:223, 1995), so it is not surprising that knock-out of FGFR2IIIb in mice leads to severe embryonic defects and lethality (De Moerlooze et al., Development 127:483, 2000).

In addition to binding FGFR1-4 with high affinity, the FGFs bind to heparin sulfate proteoglycans (HSPG) with lower affinity. In fact, binding of FGF to heparin/heparin sulfate (HS) on the cell surface is required for signalling through the FGFRs. The interaction of FGF, especially FGF2, with FGFR and heparin has been extensively studied by X-ray crystallography and mutational analysis, and it is now believed that heparin/HS participates in the formation of a symmetric 2:2 FGF-FGFR dimer (Mohammadi et al., 2005), leading to receptor activation, autophophorylation and signal transduction.

The FGFs mediate a variety of responses in various cell types including proliferation, migration and differentiation, especially during embryonic development (Omitz et al., op. cit.), and in the adult are involved in tissue homeostasis and repair. For example, FGF2 stimulates proliferation of (i.e., is mitogenic for) certain cells including fibroblasts and endothelial cells and is an anti-apoptotic survival factor for certain cells such as neural cells (Okada-Ban, op. cit.). FGF2 also stimulates differentiation (morphogenesis) and migration (motility) of endothelial cells (Dow et al., Urology 55:800, 2000). Several FGFs, especially FGF1 and FGF2, are potent angiogenic factors (Presta et al., Cytokine and Growth Factor Rev. 16:159, 2005).

The importance of the FGF system in development has been highlighted by the discovery of numerous mutations in FGFR1-3 associated with human congenital skeletal disorders including the craniosynostosis syndromes (premature fusion of the cranial sutures) (Wilkie et al., Cytokine Growth Factor Revs 16:187, 2005). These genetic diseases are usually dominant because the associated mutations lead to gain-of-function, often by facilitating receptor dimerization. Notably, the severe craniosynostosis disorder Apart syndrome (AS) is associated with one of two mutations (Ser-252→Trp or Pro-253→Arg) in the conserved D2-D3 linker region of FGFR2 that increase ligand binding affinity (Ibrahimi et al., Proc. Natl. Acad. Sci USA 98:7182, 2001).

FGF2 and other FGFs have been reported to play a role in cancer, both by stimulating angiogenesis and tumor cells directly (Grose at al., Cytokine Growth Factor Revs. 16:179, 2005; Presta et al., op cit.). FGFR2IIIb RNA is expressed in many types of tumors (Finch et al., J. Natl, Cancer Inst. 98:812, 2006), often as a consequence of its expression in the corresponding normal tissues (Orr-Urtreger et al., Dev. Biol. 158:475, 1993). KGF (FGF7) and KGFR (FGFR2IIIb) are overexpressed in many pancreatic cancers (Ishiwata et al., Am. J. Pathol. 153: 213, 1998), and their coexpression correlates with poor prognosis (Cho et al., Am. J. Pathol. 170:1964, 2007). Somatic mutations of the FGFR2 gene were found in 12% of a large panel of endometrial (uterine) carcinomas, and in several tested cases were required for tumor cell survival (Dutt et al., Proc. Natl. Acad. Sci. USA 105:8713, 2008). In two tumors the FGFR2 mutation was found to be the same S252W substitution associated with Apert syndrome. Amplification and overexpression of FGFR2 is strongly associated with the undifferentiated, diffuse type of gastric cancer, which has a particularly poor prognosis, and inhibition of the FGFR2 activity by small molecule compounds potently inhibited proliferation of such cancer cells (Kunii et al., Cancer Res. 68:2340, 2008; Nakamura et al., Gastroenterol. 131:1530, 2006). FGFR2IIIb RNA was expressed in 16/20 epithelial ovarian cancers (EOCs) but not in normal ovarian surface epithelium (Steele et al., Oncogene 20:5878, 2001); and the FGFR2IIIb ligands FGF1, FGF7 and FGF10 induced proliferation, motility and protection form cell death in EOC cell lines (Steele at al., Growth Factors 24:45, 2006), suggesting that FGFR2IIIb may contribute to the malignant phenotype in ovarian cancer.

Only a limited number of monoclonal antibodies to FGFR2 have been reported. Fortin et al. (J. Neurosci. 25:7470, 2005) reported a blocking antibody to FGFR2, and Wei et al. (Hybridoma 25: 115, 2006) developed two mAbs specific for the IIIb form of FGFR2 (i.e, KGFR) that inhibited KGF-induced cell proliferation. Yayon et al. (WO2007/144893, 2006) disclosed an inhibitory mAb that binds both FGFR2 and FGFR3. R&D Systems has marketed since 2005 an anti-FGFR2 mAb that neutralizes activity in their assay, with preference for the IIIb form. However, there have been no reports of anti-tumor activity of antibodies against FGFR2 in vivo.

SUMMARY OF THE INVENTION

In one embodiment, the invention provides a monoclonal antibody (mAb) to human fibroblast growth factor receptor 2 (FGFR2) that inhibits growth of a human tumor xenograft in a mouse. The mAb may inhibit at least one, and preferably several or all biological activities of the receptor, including binding to the receptor by FGF2. The mAb can bind to either or both of the FGFR2IIIb and FGFRIIIc forms of the receptor, e.g., to FGFR2IIIb but not to FGFR2IIIc Preferably, the mAb of the invention is genetically engineered, for example, chimeric, humanized or human. Exemplary antibodies are GAL-FR21, GAL-FR22, and GAL-FR23 and their chimeric and humanized forms, and mAbs which have the same epitope or compete for binding with one of these mAbs. In another embodiment, a pharmaceutical composition comprising a genetically engineered anti-FGFR2 antibody, e.g., chimeric or humanized GAL-FR21, GAL-FR22, and GAL-FR23, is provided. In a third embodiment, the pharmaceutical composition is administered to a patient to treat cancer or other disease, for example gastric cancer.

Exemplified humanized antibodies comprise a humanized light chain comprising CDRs from the sequence in FIG. 13A (GAL-FR21; SEQ ID NO:1) and a humanized heavy chain comprising CDRs from the sequence of FIG. 13B (GAL-FR21; SEQ ID NO:4), or comprise a humanized light chain comprising CDRs from the sequence in FIG. 16A (GAL-FR22; SEQ ID NO:7) and a humanized heavy chain comprising CDRs from the sequence of FIG. 16B (GAL-FR22; SEQ ID NO:8). Some humanized antibodies comprise the three light chain CDRs shown in FIG. 13A (GAL-FR21) and the three heavy chain CDRs shown in FIG. 13B (GAL FR21), or comprise the three light chain CDRs shown in FIG. 16A (GAL-FR22) and the three heavy chain CDRs shown in FIG. 16B (GAL-FR22). Optionally, the light chain variable region has at least 95% sequence identity to the sequence shown in FIG. 13A (HuGAL-FR21; SEQ ID NO:2) and the heavy chain variable region has at least 95% sequence identity to the sequence shown in FIG. 13B (HuGAL-FR21; SEQ ID NO:5). In some such antibodies, residues H27, H28, H30, H48, and H67 by Kabat numbering are occupied by the residue occupying the corresponding position of the heavy chain shown in FIG. 13B (GAL-FR21). A preferred humanized antibody comprises a light chain variable region having the sequence shown in FIG. 13A (HuGAL-FR21; SEQ ID NO:2) and a heavy chain variable region having the sequence shown in FIG. 13B (HuGAL-FR21; SEQ ID NO:5).

BRIEF DESCRIPTION OF THE DRAWINGS

FIG. 2. Summary of properties of the anti-FGFR2 mAbs GAL-FR21. GAL-FG22, GAL-FR23 as described under Examples.

FIG. 10. Growth of SNU-16 (A, upper panel) or OCUM-2M (B, lower panel) human gastric tumor xenografts in mice treated with PBS alone, GAL-FR21 or GAL-FR22.

FIG. 11. Binding ELISA of GAL-FR21 (upper panel) or GAL-FR22 (lower panel) to human and mouse FGFR2IIIb.

FIG. 12. Binding ELISA of GAL-FR21 (upper panel) or GAL-FR22 (lower panel) to human and cynomolgus monkey FGFR2IIIb.

FIG. 13. Amino acid sequences of the HuGAL-FR21 light chain (A) and heavy chain (B) mature variable regions (SEQ ID NOS:2 and 5) are shown aligned with mouse GAL-FR21 (SEQ ID NOS:1 and 4) and human acceptor V regions (SEQ ID NOS:3 and 6). The CDRs are underlined in the GAL-FR21 sequences, and the amino acids substituted with mouse amino acids are double underlined in the HuGAL-FR21 sequences. The 1-letter amino acid code and Kabat numbering system are used for both the light and heavy chain in the figure. Sequential numbering is used in the SEQ ID NOS.

FIG. 14. Amino acid sequences of the entire mature HuGAL-FR21 antibody light chain (A) and heavy chain (B) (SEQ ID NOS:9 and 10). The first amino acid on each line is numbered; the numbering is sequential. In the light chain, the first amino acid of the Cκ region is underlined, and in the heavy chain, the first amino acids of the CH1, hinge, CH2 and CH3 regions are underlined.

FIG. 16. Amino acid sequences of the GAL-FR22 light chain (A) and heavy chain (B) mature variable regions (SEQ ID NOS. 7 and 8), with the CDRs underlined. The 1-letter amino acid code and Kabat numbering system are used for both the light and heavy chain in the figure. Sequential numbering is used for the SEQ ID NOS.

DETAILED DESCRIPTION OF THE PREFERRED EMBODIMENTS

Figure 1:
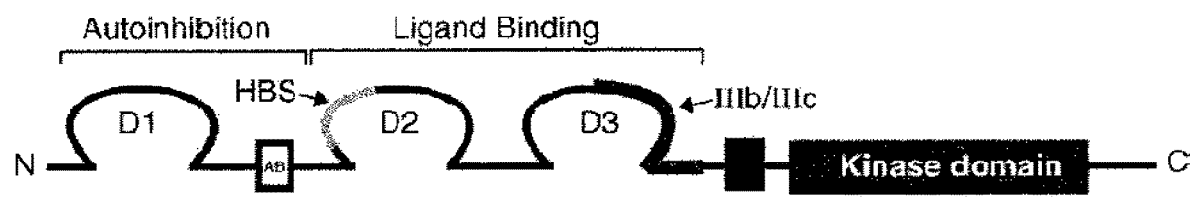
FIG. 1. Schematic diagram of the structure of FGFR2, showing the three Ig-like domains (D1, D2 and D3), transmembrane domain (black box), and intracellular kinase domain. The heparin binding site (HBS), acid box (AB) and alternative IIIb/IIIc partial domains are indicated. N=amino terminus, C=carboxy terminus.

The invention provides anti-FGFR2 monoclonal antibodies (mAbs) that inhibit biological activities of FGFR2 and/or inhibit growth of an FGFR2-expressing tumor xenograft in a mouse, pharmaceutical compositions comprising the mAbs, and methods of using them for the treatment of disease.

1. Antibodies

Antibodies are very large, complex molecules (molecular weight of ~150.000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined by Kabat. E. et al., Sequences of Proteins of Immunological Interest, U.S. Department of Health and Human Services, 1983, 1987. The part of a variable region not contained in the CDRs is called the framework, which forms the environment for the CDRs.

A humanized antibody is a genetically engineered antibody in which the CDRs from a mouse antibody ("donor antibody", which can also be rat, hamster or other non-human species) are grafted onto a human antibody ("acceptor antibody"). The sequence of the acceptor antibody can be, for example, a mature human antibody sequence, a consensus sequence of human antibody sequences, or a germline region sequence. Thus, a humanized antibody is an antibody having CDRs from a donor antibody and variable region framework and constant regions from a human antibody. In addition, in order to retain high binding affinity, at least one of two additional structural elements can be employed. See, U.S. Pat. Nos. 5,530,101 and 5,585,089, incorporated herein by reference, which provide detailed instructions for construction of humanized antibodies. Although humanized antibodies often incorporate all six CDRs (preferably as defined by Kabat, but often also including hypervariable loop H1 as defined by Chothia) from a mouse antibody, they can also be made with less than the complete CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al. Journal of Immunology. 164:1432-1441, 2000).

Similarly, it may be necessary to incorporate only part of the CDRs, namely the subset of CDR residues required for binding, termed the SDRs, into the humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies at positions in which one or more donor CDR residues is absent, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Thus, typically a humanized antibody comprises (i) a light chain comprising CDRs (often three CDRs) from a mouse antibody, e.g., GAL-FR21, a human variable region framework, and a human constant region; and (ii) a heavy chain comprising CDRs (often three CDRs) from the mouse antibody. e.g., GAL-FR21, a human variable region framework, and a human constant region. The light and heavy chain variable region frameworks may each be a mature human antibody variable region framework sequence, a germline variable region framework sequence (combined with a J region sequence), or a consensus sequence of human antibody variable region framework sequences.

In the first structural element mentioned above, the framework of the heavy chain variable region of the humanized antibody is chosen to have maximal sequence identity (between 65% and 95%) with the framework of the heavy chain variable region of the donor antibody, by suitably selecting the acceptor antibody from among the many known human antibodies. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are chosen on the basis of their ability to interact with the CDRs. For example, the replaced amino acids can be adjacent to a CDR in the donor antibody sequence or within 4-6 angstroms of a CDR in the humanized antibody as measured in 3-dimensional space.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791: and Winter, FEBS Lett. 23:92, 1998, each of which is incorporated herein by reference) or using transgenic animals (Lonberg et al., WO93/12227; Kucherlapati WO91/10741, each of which is incorporated herein by reference).

As used herein, the term "human-like" antibody refers to a mAb in which a substantial portion of the amino acid sequence of one or both chains (e.g., about 50% or more) originates from human immunoglobulin genes. Hence, human-like antibodies encompass but are not limited to chimeric, humanized and human antibodies. As used herein, a mAb with "reduced-immunogenicity" is one expected to have significantly less immunogenicity than a mouse antibody when administered to human patients. Such antibodies encompass chimeric, humanized and human mAbs as well as mAbs made by replacing specific amino acids in mouse antibodies that may contibute to B- or T-cell epitopes, for example exposed residues (Padlan, Mol. Immunol. 28:489, 1991). As used herein, a "genetically engineered" mAb is one for which the genes have been constructed or put in an unnatural environment (e.g., human genes in a mouse or on a bacteriophage) with the help of recombinant DNA techniques, and would therefore, e.g., not encompass a mouse mAb made with conventional hybridoma technology.

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 8,072,035 and 5,639,641.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

2. Anti-FGFR2 Antibodies

A monoclonal antibody (mAb) that binds FGFR2 (i.e., an anti-FGFR2 mAb) is said to neutralize FGFR2, or to be neutralizing (or inhibitory or antagonist), if the binding partially or completely inhibits one or more biological activities of FGFR2. Among the biological activities of FGFR2 that a neutralizing antibody may inhibit or block is the ability of FGFR2 to bind to one or more or all of its FGF ligands. e.g. FGF1 and/or FGF2. For FGFRIIIb these ligands encompass FGF1, FGF7 (KGF) and the other members of the FGF7 subfamily FGF3, FGF10 and FGF22. For FGFRIIIc these ligands encompass FGF1 and FGF2; FGF4 and the other members of the FGF4 subfamily FGF5 and FGF6; FGF and the other members of the FGF8 subfamily FGF17 and FGF18; and FGF9 and the other members of the FGF9 subfamily FGF16 and FGF20. Another important activity of FGFR2 that may be inhibited by a neutralizing anti-FGFR2 mAb is stimulation of proliferation of cells, e.g., epithelial or endothelial cells, fibroblasts, cells such as Ba/F3 cells into which FGFR2 has been transfected, and various human tumor cells. Other activities inhibitable by a neutralizing anti-FGFR2 mAb are stimulation of differentiation and migration of cells such as endothelial cells, and induction of angiogenesis, for example as measured by stimulation of human vascular endothelial cell (HUVEC) proliferation or tube formation or by induction of blood vessels when applied to the chick embryo chorioallantoic membrane (CAM). Usually, the neutralizing mAb inhibits these activities when induced by one or more of the FGFs listed above. Similarly, the mAb preferably inhibits all or part of the signal transduction pathway stimulated by binding of an FGF ligand to FGFR2 (Dailey et al., Cytokine Growth Factor Revs 16:233, 2005), e.g., phosphorylation of FGFR2 and downstream MAP kinases.

A neutralizing mAb of the invention at a concentration of, e.g., 0.01, 0.1, 0.5, 1, 2, 5, 10, 20 or 50 µg/ml inhibits a biological function of FGFR2 by about at least 50% but preferably 75%, more preferably by 90% or 95% or even 99%, and most preferably approximately 100% (essentially completely or indistinguishably from a negative control lacking FGFR2) as assayed by methods described under Examples or known in the art. Typically, the extent of inhibition is measured when the amount of FGF ligand used is just sufficient to fully stimulate the biological activity, or is 1, 2, or 5 ng/ml or 0.01, 0.02, 0.05, 0.1, 0.5, 1, 3 or 10 µg/ml. Preferably, the mAb is neutralizing. i.e., inhibits the biological activity, when used as a single agent, but optionally 2 mAbs can be used together to give inhibition. Most preferably, the mAb neutralizes not just one but two, three or several of the biological activities listed above; for purposes herein, an anti-FGFR2 mAb that used as a single agent neutralizes all the biological activities of FGFR2 is called "fully neutralizing", and such mAbs are most preferable.

The instant invention provides neutralizing mAbs that bind FGFR2IIIb but bind less well or not detectably to FGFRIIIc, or alternatively bind to FGFR2IIIc but less well or not detectably to FGFRIIIb, or in a third alternative bind to both FGFR2IIIb and FGFR2IIIc, and the use of any of these types of antibodies in a pharmaceutical composition, especially for the treatment of cancer or other diseases. The invention also provides mAbs, either neutralizing or non-neutralizing, that bind FGFR2 in one or more of its forms and inhibit, preferably completely, growth of a tumor xenograft that expresses FGFR2, e.g., a SNU-16 or OCUM-2M xenograft. Such a mAb may inhibit tumor growth by, e.g., transmitting a negative growth signal or a pro-apoptotic signal through FGFR2. MAbs of the invention are preferably specific for FGFR2 or bind it preferentially, that is they do not bind, or only bind to a much lesser extent (e.g., at least 10-fold less), proteins that are related to FGFR2 such as the other FGF receptors FGFR1, FGFR3 and FGFR4 as well as other membrane receptor tyrosine kinases. On the other hand, in some instances, mAbs that bind one or more of the other FGF receptors in addition to FGFR2 are preferred. MAbs of the invention typically have a binding affinity (association constant $K_\alpha$) for FGFR2 of at least $10^7$ $M^{-1}$ but preferably $10^8$ $M^{-1}$ or higher, and most preferably $10^9$ $M^{-1}$ or higher or even $10^{10}$ $M^{-1}$ or higher. Mabs showing differential or preferential binding to one form of FGFR or FGFR2 over another, preferably show a preference of at least five, ten or hundred fold between the forms, e.g., as measured by $K_a$. Lack of binding between an antibody and antigen (i.e., the antibody does not bind the antigen) means any signal from an attempted binding reaction between the two is indistinguishable from a negative control, e.g., in which antibody or antigen is absent or replaced by an inactive agent.

Some mAbs of the invention bind both human FGFR2 and mouse FGFR2, or bind human FGFR2 and one, two or more or all of mouse, rat, rabbit, chicken, dog and/or monkey (e.g., cynomolgus monkey) FGFR2. In some instances, the mAb binds mouse FGFR2 (e.g., mouse FGFR2IIIb) with an affinity (i.e., $K_a$) within 2, 10 or 100-fold of that of the affinity for human FGFR2; similarly the mAb may bind cynomolgus monkey and/or chimpanzee FGFR2 (e.g., FGFR2IIIb) with an affinity within 2 or 10-fold of that of the affinity for human FGFR2 or even substantially the same as or indistinguishably from binding to human FGFR2 (i.e., within experimental error). Other mAbs are specific for only human FGFR2.

MAbs of the invention include anti-FGFR2 antibodies in their natural tetrameric form (2 light chains and 2 heavy chains) and may be of any of the known isotypes IgG, IgA, IgM, IgD and IgE and their subtypes, i.e., human IgG1, IgG2, IgG3, IgG4 and mouse IgG1, IgG2a, IgG2b, and IgG3. The mAbs of the invention also include fragments of antibodies such as Fv, Fab and F(ab')$_2$; bifunctional hybrid antibodies (e.g., Lanzaveochia et al., Eur. J. Immunol. 17:105, 1987), single-chain antibodies (Huston et al., Proc. Natl. Acad. Sci. USA 85:5879, 1988; Bird et al., Science 242:423, 1988); single-arm antibodies (Nguyen et al., Cancer Gene Ther. 10:840, 2003); and antibodies with altered constant regions (e.g., U.S. Pat. No. 5,624,821). The mAbs may be of animal (e.g., mouse, rat, hamster or chicken) origin, or they may be genetically engineered. Rodent mAbs are made by standard methods, comprising multiple immunization with FGFR2 in appropriate adjuvant i.p., i.v., or into the footpad, followed by extraction of spleen or lymph node cells and fusion with a suitable immortalized cell line, and then selection for hybridomas that produce antibody binding to FGFR2, e.g., see under Examples. Chimeric and humanized mAbs, made by art-known methods mentioned supra, are preferred embodiments of the invention. Human antibodies made. e.g., by phage display or transgenic mice methods are also preferred (see e.g., Dower et al., McCafferty et al., Winter, Lonberg et al., Kucherlapati, supra).

The anti-FGFR2 mAbs GAL-FR21, GAL-FR22 and GAL-FR23 described below are examples of the invention. Once a single, archtypal anti-FGFR2 mAb, for example GAL-FR21, has been isolated that has the desired properties described herein of neutralizing FGFR2, it is straightforward to generate other mAbs with similar properties, e.g., having the same epitope, by using art-known methods. For example, mice may be immunized with FGFR2 as described above, hybridomas produced, and the resulting mAbs screened for the ability to compete with the archtypal mAb for binding to FGFR2. Mice can also be immunized with a smaller fragment of FGFR2 containing the epitope to which the archtypal mAb binds. The epitope can be localized by, e.g., screening for binding to a series of overlapping peptides spanning FGFR2. Alternatively, the method of Jespers et al., Biotechnology 12:899, 1994 may be used to guide the selection of mAbs having the same epitope and therefore similar properties to the archtypal mAb, e.g., GAL-FR21. Using phage display, first the heavy chain of the archtypal antibody is paired with a repertoire of (preferably human)

light chains to select an FGFR2-binding mAb, and then the new light chain is paired with a repertoire of (preferably human) heavy chains to select a (preferably human) FGFR2-binding mAb having the same epitope as the archtypal mAb. Alternatively variants of, e.g., GAL-FR21 can be obtained by mutagenesis of cDNA encoding the heavy and light chains of GAL-FR21.

MAbs with the same or overlapping epitope as GAL-FR21, GAL-FG22 or GAL-FR23, e.g., that compete for binding to FGFR2 with the respective mAb, provide other examples of the invention. A chimeric or humanized form of GAL-FR21, GAL-FG22 or GAL-FR23 is an especially preferred embodiment. MAbs that are 90%, 95% or 99% identical to GAL-FR21, GAL-FG22 or GAL-FR23 in amino acid sequence of the heavy and/or light chain variable regions (not including the signal sequence) and maintain its functional properties, and/or which differ from the respective mAb by a small number of functionally inconsequential amino acid substitutions (e.g., conservative substitutions), deletions, or Insertions are also included in the invention. MAbs having at least one and preferably all six CDR(s) that are 90%, 95% or 99% or 100% identical to corresponding CDRs of GAL-FR21, GAL-FG22 or GAL-FR23 are also included. Here, as elsewhere in this application, percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

For purposes of classifying amino acid substitutions as conservative or nonconservative, amino acids may be grouped as follows: Group I (hydrophobic side chains); met, ala, val, leu, ile; Group II (neutral hydrophilic side chains): cys, ser, thr; Group III (acid side chains): asp, glu; Group IV (basic side chains): asn, gln, his, lys, arg; Group V (residues influencing chain conformation): gly, pro; and Group VI (aromatic side chains): trp, tyr, phe. Conservative substitutions involve substitutions between amino acids in the same group. Non-conservative substitutions constitute exchanging a member of one of these groups for a member of another.

Native mAbs of the invention may be produced from their hybridomas. Genetically engineered mAbs, e.g., chimeric or humanized mAbs, may be expressed by a variety of art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, poly A sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NS0, and cells expressing the antibodies selected by appropriate antibiotic selection. See, e.g., U.S. Pat. No. 5,530,101. Larger amounts of antibody may be produced by growing the cells in commercially available bioreactors.

Once expressed, the mAbs or other antibodies of the invention may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% w/w homogeneity are preferred, and 98% or 99% w/w or more homogeneity most preferred, for pharmaceutical uses.

3. Treatment Methods

The invention provides methods of treatment in which the mAb of the invention (i.e., an anti-FGFR2 MAb) is administered to patients having a disease (therapeutic treatment) or at risk of occurrence or recurrence of a disease (prophylactic treatment). The term "patient" Includes human patients; veterinary patients, such as cats, dogs and horses; farm animals, such as cattle, sheep, and pigs; and laboratory animals used for testing purposes, such as mice and rats. The methods are particularly amenable to treatment of human patients. The mAb used in methods of treating human patients binds to the human FGFR2 protein, the sequence of which is provided by GenBank Locus AF487553. Citations for other FGFRs or FGFs referenced in this disclosure are provided in the Background section. A mAb to a human protein can also be used in other species in which the species homolog has antigenic crossreactivity with the human protein. In species lacking such crossreactivity, an antibody is used with appropriate specificity for the species homolog present in that species. However, in xenograft experiments in laboratory animals, a mAb with specificity for the human protein expressed by the xenograft is generally used.

In a preferred embodiment, the present invention provides a pharmaceutical formulation comprising the antibodies described herein. Pharmaceutical formulations contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science $16^{th}$ edition, Osol, A. Ed. 1980). The mAb is typically present at a concentration of 0.1-100 mg/ml, e.g., 1-10 mg/ml or 10-50 mg/ml, for example 5, 10, 20, 30, 40, 50 or 60 mg/ml.

In another preferred embodiment, the invention provides a method of treating a patient with a disease using an anti-FGFR2 mAb in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given is sufficient to at least partially alleviate the condition being treated ("therapeutically effective dose") and optionally 0.1 to 5 mg/kg body weight, for example 1, 2, 3 or 4 mg/kg, but may be as high as 0.1 or 1 to 10 mg/kg or even 1 to any of 15, 20 or 30 mg/kg. A fixed unit dose may also be given, for example, 100, 200, 500, 1000 or 2000 mg, or the dose may be based on the patient's surface area, e.g., 1000 mg/m$^2$. Usually between 1 and 8 doses, (e.g., 1, 2, 3, 4, 5, 6, 7 or 8) are administered to treat cancer, but 10, 20 or more doses may be given. The mAb can be administered daily, biweekly, weekly, every other week, monthly or at some other interval, depending, e.g. on the half-life of the mAb, for 1 week, 2 weeks, 4 weeks, 8 weeks, 3-6 months or longer. Repeated courses of treatment are also possible, as is chronic administration.

A combination of a dose, frequency of administration and route of administration effective to at least partially alleviate a disease present in a patient being treated is referred to as therapeutically effective regime. A combination of a dose, frequency of administration and route of administration effective to inhibit or delay onset of a disease in a patient is referred to as a prophylactically effective regime.

Diseases susceptible to treatment with the anti-FGFR2 mAbs of this invention include solid tumors, especially those believed to require angiogenesis or to be associated with detectable or preferably elevated levels of FGFR2 and/or an FGF, for example ovarian cancer, endometrial cancer, breast cancer, lung cancer (small cell or non-small cell), colon cancer, prostate cancer, cervical cancer, pancreatic cancer, gastric cancer, esophageal cancer, hepatocellular carcinoma (liver cancer), renal cell carcinoma (kidney cancer), head-and-neck tumors, mesothelioma, melanoma, sarcomas, and brain tumors (e.g., gliomas, such as glioblastomas). Elevated levels can be measured at the protein or mRNA level in cancerous tissue relative to comparable levels of FGFR2 (e.g., FGFR2IIIb) or FGF (e.g., FGF2, FGF7 or FGF10) in normal tissue such as tissue-matched noncancerous tissue, preferably from the same patient. Detectable levels can be similarly measured at the protein or mRNA level in cancerous tissue and compared with background levels in control samples in which the analyte (e.g., FGFR2 or FGF) is known to be absent or relative to negative controls in which detection is performed using an antibody or primer or probe known not to bind the analyte or nucleic acid encoding the analyte. Leukemias, lymphomas, multiple myeloma and other hematologic malignancies, especially any of these cancers having detectable or elevated expression of FGFR2 and/or FGF, can also be susceptible to treatment with the anti-FGFR2 mAbs. Other diseases associated with angiogenesis for which treatment with the anti-FGFR2 mAbs of the invention are suitable include age-related macular degeneration (AMD), diabetic retinopathy, neovascular glaucoma and other diseases of the eye; psoriasis and other diseases of the skin; rheumatoid arthritis; and genetic skeletal disorders associated with mutations in the FGFR2, e.g., Apert syndrome, as described above.

In a preferred embodiment, the anti-FGFR2 mAb is administered in combination with (i.e., together with, that is, before, during or after) other therapy. For example, to treat cancer, the anti-FGFR2 mAb may be administered together with any one or more of the known chemotherapeutic drugs, for example alkylating agents such as carmustine, chlorambucil, cisplatin, carboplatin, oxaliplatin, procarbazine, and cyclophosphamide; antimetabolites such as fluorouracil, floxuridine, fludarabine, gemcitabine, methotrexate and hydroxyurea; natural products including plant alkaloids and antibiotics such as bleomycin, doxorubicin, daunorubicin, idarubicin, etoposide, mitomycin, mitoxantrone, vinblastine, vincristine, and Taxol (paclitaxel) or related compounds such as Taxotere®; the topoisomerase 1 inhibitor irinotecan; agents specifically approved for brain tumors including temozolomide and Gliadel® wafer containing carmustine; and inhibitors of tyrosine kinases such as Gleevec®, Sutent® (sunitinib malate), Nexavar® (sorafenib) and Tarceva® (erlotinib) or Iressa® (gefitinib); inhibitors of angiogenesis; and all approved and experimental anti-cancer agents listed in WO 2005/017107 A2 (which is herein incorporated by reference). The anti-FGFR2 mAb may be used in combination with 1, 2, 3 or more of these other agents used in a standard chemotherapeutic regimen. Normally, the other agents are those already known to be effective for the particular type of cancer being treated. The anti-FGFR2 mAb is especially useful in overcoming resistance to chemotherapeutic drugs and thereby increasing their effectiveness.

Other agents with which the anti-FGFR2 mAb can be administered to treat cancer include biologics such as monoclonal antibodies, including Herceptin™ against the HER2 antigen; Avastin® against VEGF; or antibodies to the Epidermal Growth Factor (EGF) receptor such as Erbitux® (cetuximab) and Vectibix® (panitumumab). Antibodies against Hepatocyte Growth Factor (HGF) are especially preferred for use with the anti-FGFR2 mAb, including mAb L2G7 (Kim et al., Clin Cancer Res 12:1292, 2006 and U.S. Pat. No. 7,220,410) and particularly its chimeric and humanized forms such as HuL2G7 (WO 07115049 A2); the human anti-HGF mAbs described in WO 2005/017107 A2, particularly 2.12.1; and the HGF binding proteins described in WO 07143090 A2 or WO 07143098 A2; and other neutralizing anti-HGF mAbs that compete for binding with any of the aforementioned mAbs. A mAb that binds the cMet receptor of HGF is also preferred, for example the anti-cMet mAb OA-5D5 (Martens et al., Clin. Cancer Res. 12:6144, 2006) that has been genetically engineered to have only one "arm", i.e. binding domain. Antibodies against the other FGFR receptors FGFR1, 3, 4 or against various FGFs such as FGF1, FGF2 and FGF7 are also preferred for use in combination with the anti-FGFR2 mAb. Moreover, the anti-FGFR2 mAb can be used together with any form of surgery and/or radiation therapy including external beam radiation, intensity modulated radiation therapy (IMRT) and any form of radiosurgery such as, e.g. Gamma Knife.

Treatment (e.g., standard chemotherapy) including the anti-FGFR2 mAb antibody may alleviate a disease by increasing the median progression-free survival or overall survival time of patients with cancer by at least 30% or 40% but preferably 50%, 60% to 70% or even 100% or longer, compared to the same treatment (e.g., chemotherapy) but without the anti-FGFR2 mAb, or increase either of these times by 2 weeks, 1, 2 or 3 months, or preferably by 4 or 6 months or even 9 months or a year. In addition or alternatively, treatment (e.g., standard chemotherapy) including the anti-FGFR2 mAb may increase the complete response rate, partial response rate, or objective response rate (complete+ partial) of patients with these tumors (e.g., ovarian, gastric, endometrial, pancreatic, breast, lung, colon and glioblastomas especially when relapsed or refractory) by at least 30% or 40% but preferably 50%, 60% to 70% or even 100% compared to the same treatment (e.g., chemotherapy) but without the anti-FGFR2 mAb.

Typically, in a clinical trial (e.g., a phase II, phase II/III or phase III trial), the aforementioned increases in median progression-free survival and/or response rate of the patients treated with chemotherapy plus the anti-FGFR2 mAb, relative to the control group of patients receiving chemotherapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

4. Other Methods

The anti-FGFR2 mAbs of the invention also find use in diagnostic, prognostic and laboratory methods. They may be used to measure the level of FGFR2 in a tumor or in the circulation of a patient with a tumor, and therefore to follow and guide treatment of the tumor. For example, a tumor associated with high levels of FGFR2 (e.g., increased relative to tissue-matched noncancerous sample from the same patient) are especially susceptible to treatment with an anti-FGFR2 mAb. In particular embodiments, the mAbs can be used in an ELISA or radioimmunoassay to measure the level of FGFR2, e.g. in serum, or in immunohistochemistry to localize FGFR2 expression, e.g., in a tumor biopsy specimen. The use of two anti-FGFR2 mAbs binding to different epitopes (i.e., not competing for binding) is especially useful in developing a sensitive "sandwich" ELISA to detect FGFR2. For various assays, the mAb may be labeled with fluorescent molecules, spin-labeled molecules, enzymes or radioisotopes, and may be provided in the form of kit with all the necessary reagents to perform the assay for FGFR2. In other uses, the anti-FGFR2 mAbs are used to purify FGFR2. e.g., by affinity chromatography.

EXAMPLES

Example 1: Reagents and Assays

Preparation of Flag-FGF1, FLAG-FGF2, and FLAG-FGF7.

The DNA sequence for human FGF1 (the form with 155 amino acids; Chiu et al., Oncogene 5:755-1990) and human FGF2 (the form with 155 amino acids; Sommer et al., Biochem. Biophys. Res. Comm. 144:543, 1987) were synthesized (GenScript, Inc), then PCR amplified to have a N-terminal Flag peptide tag and cloned into a derivative of the pET vector (Invitrogen) using standard molecular biology techniques. These plasmids were transformed into *E. coli* BL21 (DE3) cells and FGF1 or FGF2 expression was induced using 1 mM IPTG. The level of FGF expression was determined using an FGF1 or FGF2 specific ELISA kit (R&D Systems). FGF was purified using heparin-Sepharose CL-6B beads (Amersham Biosciences) as described (Wiedlocha at al., Mol. Cell. Biol., 16:270, 1996). Similarly, a gene for human FGF7 (the precursor form with 194 amino acids; Finch, P. W. et al., Science 245:752, 1989) was synthesized and PCR amplified to have a N-terminal Flag tag in a pCMV vector (a derivative of pDrive, Invitrogen), and Flag-FGF10 was made in an analogous way. Plasmid DNAs were transfected into human 293F cells. Culture supernatant of the transfected 293F cells was used for the ligand-receptor binding assay.

Preparation of FGFR2 Fusion Proteins.

The extracellular domain (ECD) of human FGFR2IIIb and human FGFR2IIIc were expressed as immunoadhesin molecules. For the alpha forms, the DNA fragments encoding the entire ECD of FGFR2IIIb (amino acids 1-378) or FGFR2IIIc (amino acids 1-377) were fused to human Fc (residues 216 to 446) via a polypeptide linker; for the beta forms (missing D1) amino acids 152-378 for FGFR2(beta) IIIb and amino acids 152-377 for FGFR2(beta)IIIc were used instead. These FGFR2-Fc molecules were expressed by transfecting 293F cells and selecting stable transfectants in the presence of G418 (1 mg/ml) in 293 expression medium (Invitrogen). The FGFR2-Fc secreted from 293F transfected cells was purified using a protein A/G column. Similarly, cDNA of the cynomolgus (cyno) monkey FGFR2 ECD was cloned by standard techniques from cyno liver mRNA, and amino acids 1-378 were fused to human Fc to create cyno FGFR2IIIb-Fc for expression. Chimpanzee FGFR2IIIb-Fc was constructed by using in vitro mutagenesis to convert the one amino acid in the human FGFR2IIIb ECD that differs from chimp FGFR2IIIb into the chimp amino acid (residue 186 methionine to threonine, based on the known sequences in GenBank). Mouse FGFR2(beta)IIIb-Fc protein was purchased from R&D Systems (Catalog #708-MF).

ELISA Assay for mAb Binding to FGFR2 Fusion Protein.

ELISA plates were coated with goat anti-human IgG-Fc (2 µg/ml) overnight at 4° C. Then nonspecific binding sites were blocked with 2% BSA for 1 hr at RT. Plates were incubated with one of the FGFR2 fusion proteins described above (1 µg/ml) for 1 hr, followed by incubation with various concentrations of mAbs or hybridoma culture fluids for 1 hr. The bound mAb was detected with HRP-Goat anti-mouse antibody followed by washing, addition of TMB substrate (Sigma) and reading at 450 nm. In all ELISA assays, plates were washed 3 times between each step.

Flow Cytometry.

After washing twice in cell sorting buffer (CSB: PBS/1% FBS/0.02% $NaN_3$), $2\times10^5$ cells were resuspended in 50 µl of CSB in a microtiter well and incubated with 50 µl of the anti-FGFR2 mAb to be tested (1 µg/50 µl) for 1 hr on ice. Cells were then washed twice in CSB and the bound antibodies detected by incubation with FITC-goat anti-mouse IgG (Jackson ImmunoResearch Laboratories) for 1 hr on ice. After washing twice in CSB, cells were analyzed on a FACScan (Becton Dickinson).

Example 2: Generation of Monoclonal Antibodies to FGFR2

Balb/c mice (5-6 week old female) were immunized by injection in their rear footpads at 1 week intervals either 20 or 22 times with FGFR2(beta)IIIb-Fc (initial dose 10 µg/footpad, then 5 µg/footpad), or with 17 doses FGFR2IIIc-Fc (initial dose 10 µg/footpad, then 5 doses at 2 µg, then at 5 µg) followed by 5 doses FGFR2(beta)IIIc-Fc (at 5 µg/footpad), with the antigen suspended in MPL/TDM (Sigma-Aldrich). Three days after the final injection, popliteal lymphoid cells were extracted and fused with P3/X63-Ag8U1 mouse myeloma cells at a 1:1 ratio using a Hybrimune Electrofusion System (Cyto Pulse Sciences). Hybridomas were selected by the addition of 2×HAT (Sigma) 24 hr later. Ten days after the fusion, hybridoma culture supernatants were screened for their ability to bind to FGFR2IIIb-Fc but not to human IgG using ELISA. Selected mAbs were then screened for their ability to recognize FGFR2IIIb on the human gastric tumor cell line SNU-16 (Shin et al, J. Cancer Res. Clin. Oncol. 126:519, 2000). Selected hybridomas were then cloned twice using the limiting dilution technique. Three mAbs selected in this way wore GAL-FR21 and GAL-FR22 from the first immunization regime, and GAL-FR23 from the second immunization regime. Properties of these mAbs are shown in FIG. 2 as further described below.

In addition, a number of other anti-FGFR2 mAbs were obtained from the fusions, including FR2bB 100.12.9, FR2bC 54.8.11, FR2bC 100.7.9, FR2bC 101.8.2, FR2bC 115.1.5, FR2bC 149.8.8, FR2bB 11.5.3, and FR2bB 18.1.6.

Example 3: Properties of the Anti-FGFR2 mAbs

Figure 3:
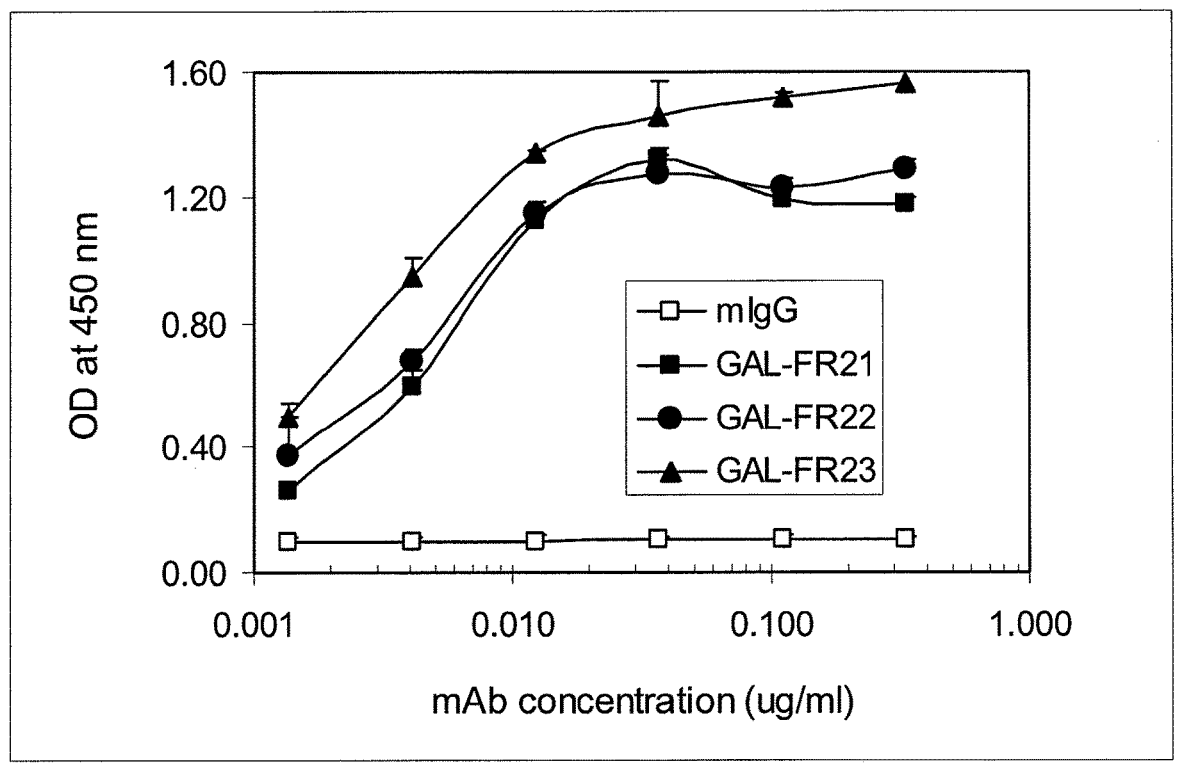
FIG. 3. Binding ELISA of mAbs GAL-FR21, GAL-FR22 and GAL-FR23 and negative control mIgG to FGFR2IIIb.
Figure 4:
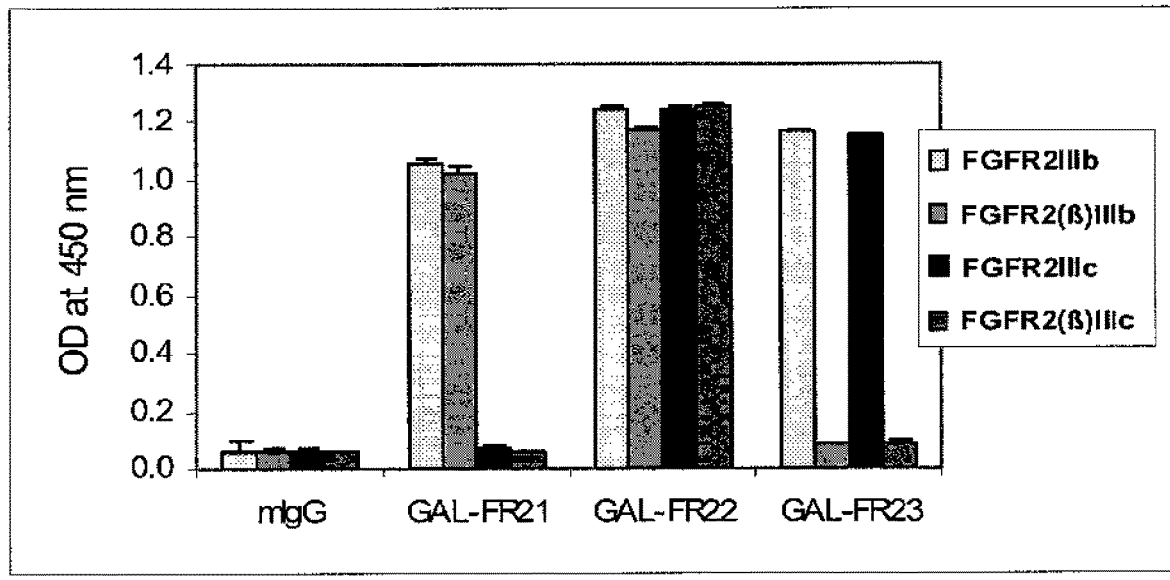
FIG. 4. Binding ELISA of mAbs GAL-FR21, GAL-FR22 and GAL-FR23 and negative control mouse mAb 5G8 to each of the four forms of FGFR2—FGFR2IIIb, FGFR2(beta)IIIb, FGFR2(IIIc) and FGFR2(beta)IIIc—as fusion proteins with Fc. A fixed concentration of each mAb was used in the assay.

As seen in FIG. 3, all three selected mAbs GAL-FR21, GAL-FR22 and GAL-FR23 bind well to FGFR2IIIb in the ELISA assay described in Example 1. By using the four different forms of FGFR2-Fc in the ELISA, it was determined that each of these mAbs has a different binding pattern and therefore epitope (FIG. 4). GAL-FR21 binds to both the alpha and beta forms of FGFR2IIIb (i.e., with and without D1), but not to FGFRIIIc. The epitope therefore cannot involve D1 and must involve D3IIIb, so is likely encompassed within D3IIIb or D3. GAL-FR22 also binds to both alpha and beta forms, but in both the IIIb and IIIc context, so the epitope is presumably encompassed in D2-D3IIIa or certainly D2-D3. Finally, GAL-FR23 does not bind to either of the beta forms, so its epitope must be wholly or partially in D1. Hence, mAbs that have an epitope either in D1 or D2-D3 or D3 are encompassed in the instant invention.

Figure 5:
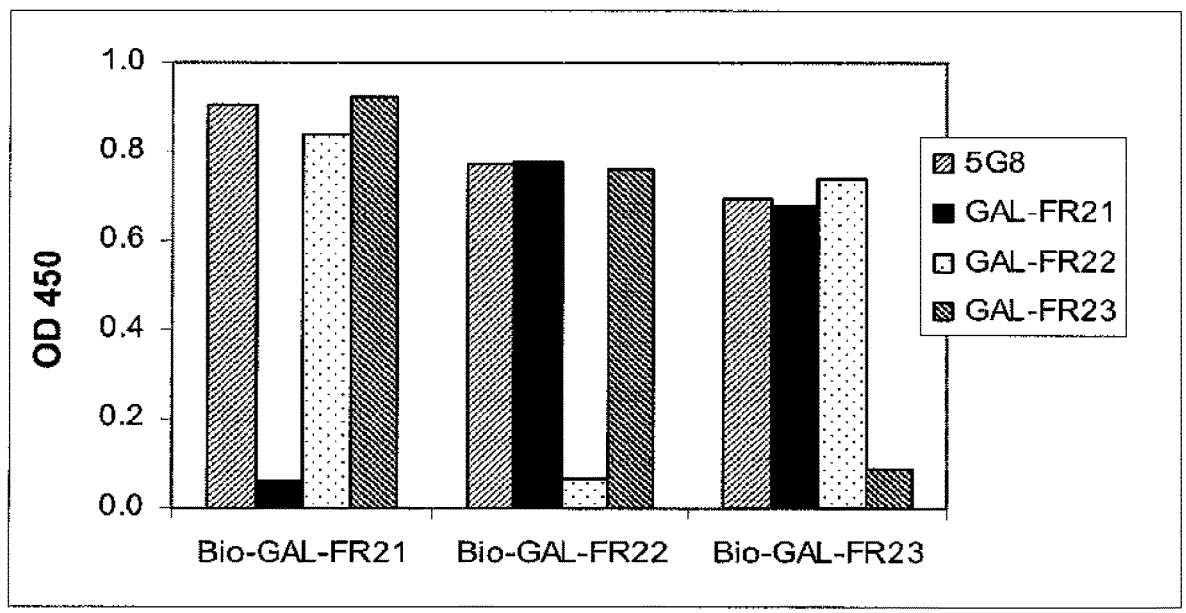
FIG. 5. Competitive binding ELISA to FGFR2IIIb of each of the mAbs GAL-FR21, GAL-FR22 and GAL-FR23 and negative control mouse mAb 5G8 against the mAbs in biotinylated form. A 100:1 ratio of unlabeled to biotinylated mAb was used.

To confirm that the mAbs GAL-FR21, GAL-FR22 and GAL-FR23 bind to different epitopes, a competition experiment was performed in which each mAb was biotinylated, and then 0.4 μg of the biotinylated mAb was competed with a 100:1 excess of each of the other unlabeled mAbs (or control murine mAb 5G8) for binding to FGFR2IIIb-Fc in the ELISA assay described above (but with HRP-streptavidin as the detection reagent). As seen in FIG. 5, each mAb competed with itself for binding but not with the other mAbs, showing that they have different epitopes. In addition, the other mAbs FR2bB 100.12.9. FR2bC 54.8.11. FR2bC 100.7.9, FR2bC 101.8.2. Fr2bC 115.1.5, FR2bC 149.8.8 competed for binding with biotinylated GAL-FR21 In this assay so have the same or overlapping epitope as GAL-FR21, while the mAbs FR2bB 11.5.3, and FR2bB 18.1.6 competed for binding with biotinylated GAL-FR22 so have the same or overlapping epitope as GAL-FR22.

Figure 6:
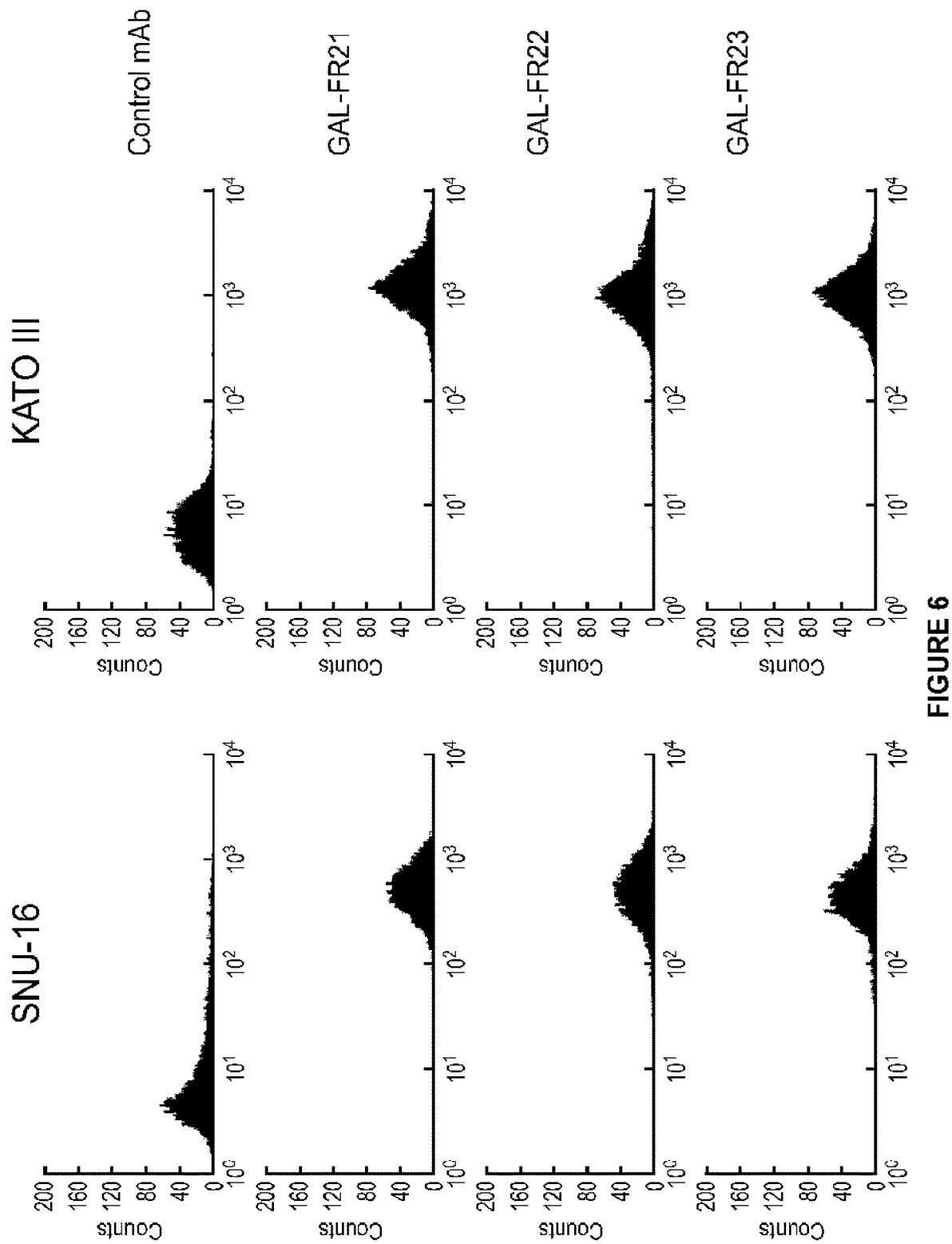
FIG. 6. Flow cytometry of binding of the mAbs GAL-FR21, GAL-FR22 and GAL-FR23 and negative control mAb to FGFR2IIIb on SNU-16 and KATO III cells.
Figure 7:
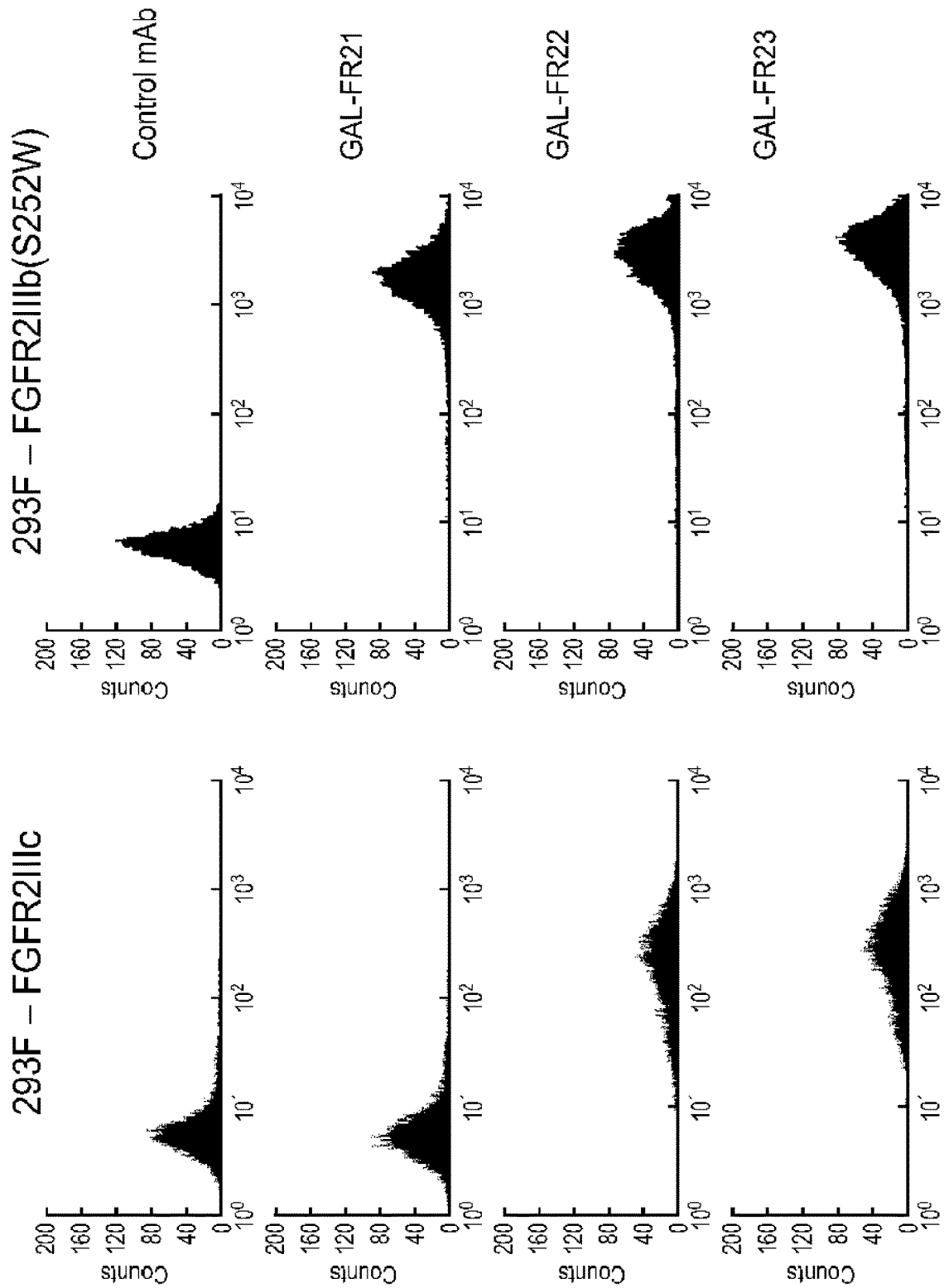
FIG. 7. Flow cytometry of the mAbs GAL-FR21, GAL-FR22 and GAL-FR23 and negative control mAb binding to 293F cells transfected with FGFR2IIIc or FGFR2IIIb (S252W).

To confirm that the selected mAbs bind to the appropriate forms of FGFR2 on the cell membrane, flow cytometry was employed. KATO-III (ATCC HTB-103) and SNU-16 (ATCC CRL-5974) cells, which overexpress FGFR2IIIb, were used to test binding to that form of the receptor. As seen in FIG. 6, all three mAbs GAL-FR21, GAL-FR22 and GAL-FR23 bind both cell lines, as expected from their epitopes described above. Human 293F cells transfected with a gene for FGFRIIIc were used to test binding to that form, after verifying that none of the mAbs bind to the host 293F cells themselves. As seen in FIG. 7, GAL-FR22 and GALFR23 but not GALFR21 bind to the FGFRIIIb-transfected cells, as expected from their epitopes. Finally, since the S252W mutation of FGFR2 is found in some cancer cells, binding of the mAbs to 293F cells transfected with an FGFR2IIIb gene constructed to contain that mutation (FGFR2IIIb(S252W)) was tested. As also seen in FIG. 7, all the mAbs bound to the FGFR2IIIb(S252W)-transfected cells. The ability to bind FGFR2IIIb(S252W) is a preferred property of mAbs of the invention.

Figure 8A:
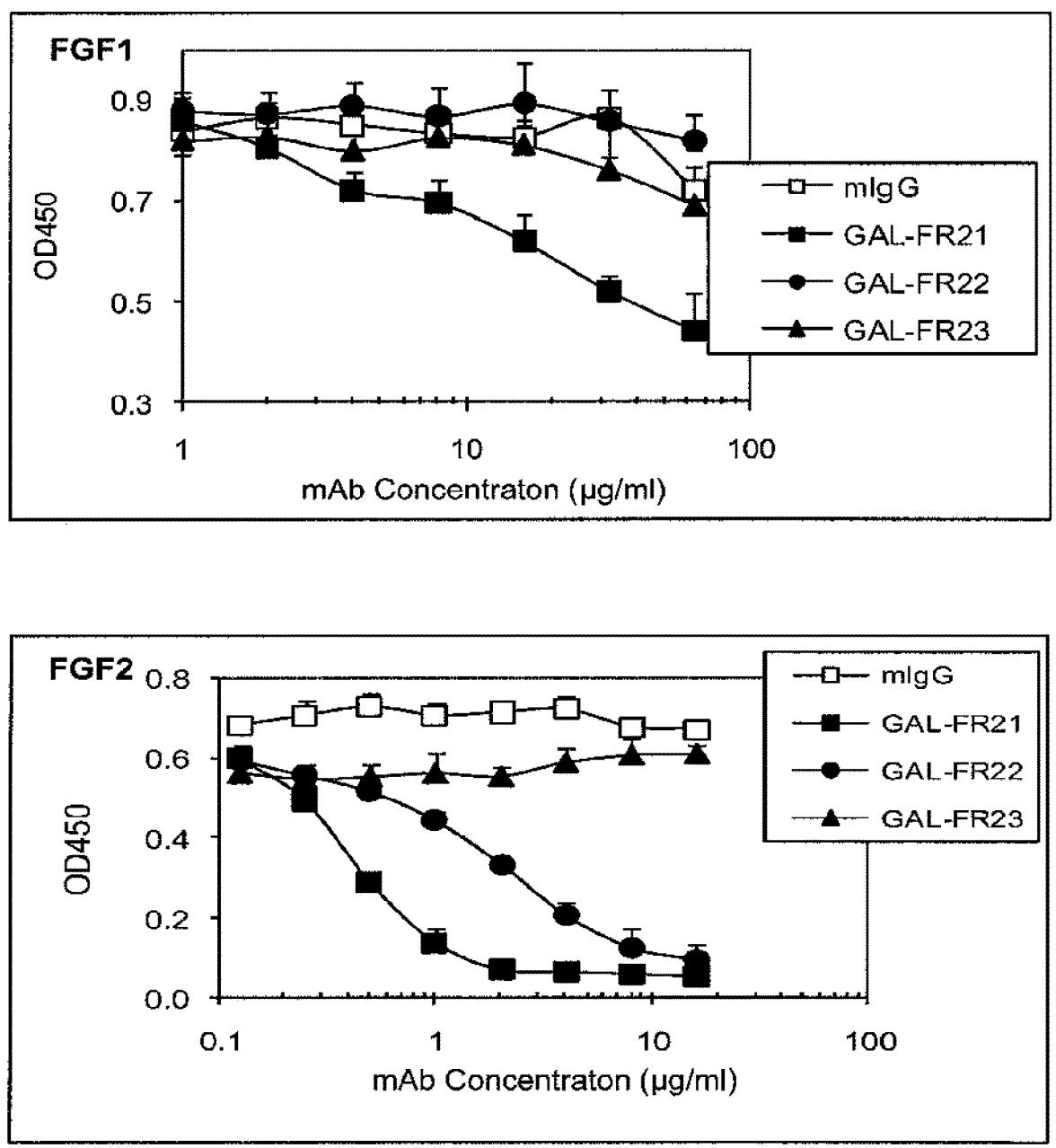
FIGS. 8A and B. (A) ELISA assay measuring inhibition of binding of FGF1 (upper panel) and FGF2 (lower panel) to FGFR2IIIb by mAbs GAL-FR21, GAL-FR22 and GAL-FR23. (B) ELISA assay measuring inhibition of binding of FGF7 (upper panel) and FGF10 (lower panel) to FGFR2IIIb by mAbs GAL-FR21 and GAL-FR22. For (A) and (B), mIgG is negative control mouse mAb.

To determine the ability of the mAbs to inhibit binding of FGF ligands to FGFR2, an ELISA assay was used. ELISA wells were coated with 2 μg/ml of goat anti-human IgG-Fc overnight at 4° C. After blocking with 2% BSA for 1 hr at RT, the wells were incubated with 0.5 μg/ml of FGFR2IIIb-Fc for 1 hr, followed by incubation with Flag-FGF1 or Flag-FGF2 (0.2 μg/ml) in the presence of various concentrations of mAbs for 1 hr. The bound Flag-FGF was detected by the addition of HRP-anti-Flag M2 antibody (Sigma) and then addition of TMB substrate. As can be seen from FIG. 8A, the mAb GAL-FR21 weakly blocked binding of FGF1 to FGFR2IIIb in this assay, but GAL-FR22 and GAL-FR23 did not block FGF1 binding. In contrast GAL-FR21 strongly blocked binding of FGF2 to FGFR2IIIb, GAL-FR22 moderately blocked FGF2 binding, and GAL-FR23 did not block binding. In similar assays but using Flag-FGF7 and Flag-FGF10, it was also shown (FIG. 8B) that GAL-FR21 and GAL-FR22 block binding of FGF7 and FGF10 to FGFR2IIIb. Indeed, advantageous mAbs of the invention, like GAL-FR21 and GAL-FR22, block binding of FGF2 and FGF7 and/or FGF10 to FGFR2IIIb, preferably by 80% or 90% or 95% or completely or essentially completely. Hence GAL-FR21 and GAL-FR22 but not GAL-FR23 have been shown to neutralize at least one biological activity of FGFR2.

Example 4: Xenograft Models

Xenograft experiments are carried out as described previously (Kim et al., Nature 362:841, 1993). Human tumor cells typically grown in complete DMEM medium are harvested in HBSS. Female athymic nude mice or NIH-III Xid/Beige/nud mice (4-6 wks old) are injected subcutaneously with 2-10×10$^6$ cells in 0.1 ml of HBSS in the dorsal areas. When the tumor size reaches 50-100 mm$^3$, the mice are grouped randomly and 5 mg/kg (100 μg total) or some other dosage of mAbs are administered i.p. twice per week in a volume of 0.1 ml. Tumor sizes are determined twice a week by measuring in two dimensions [length (a) and width (b)]. Tumor volume is calculated according to $V=ab^2/2$ and expressed as mean tumor volume±SEM. The number of mice in each treatment group is typically 5-7 mice. Statistical analysis can be performed, e.g., using Student's t test.

Figure 9:
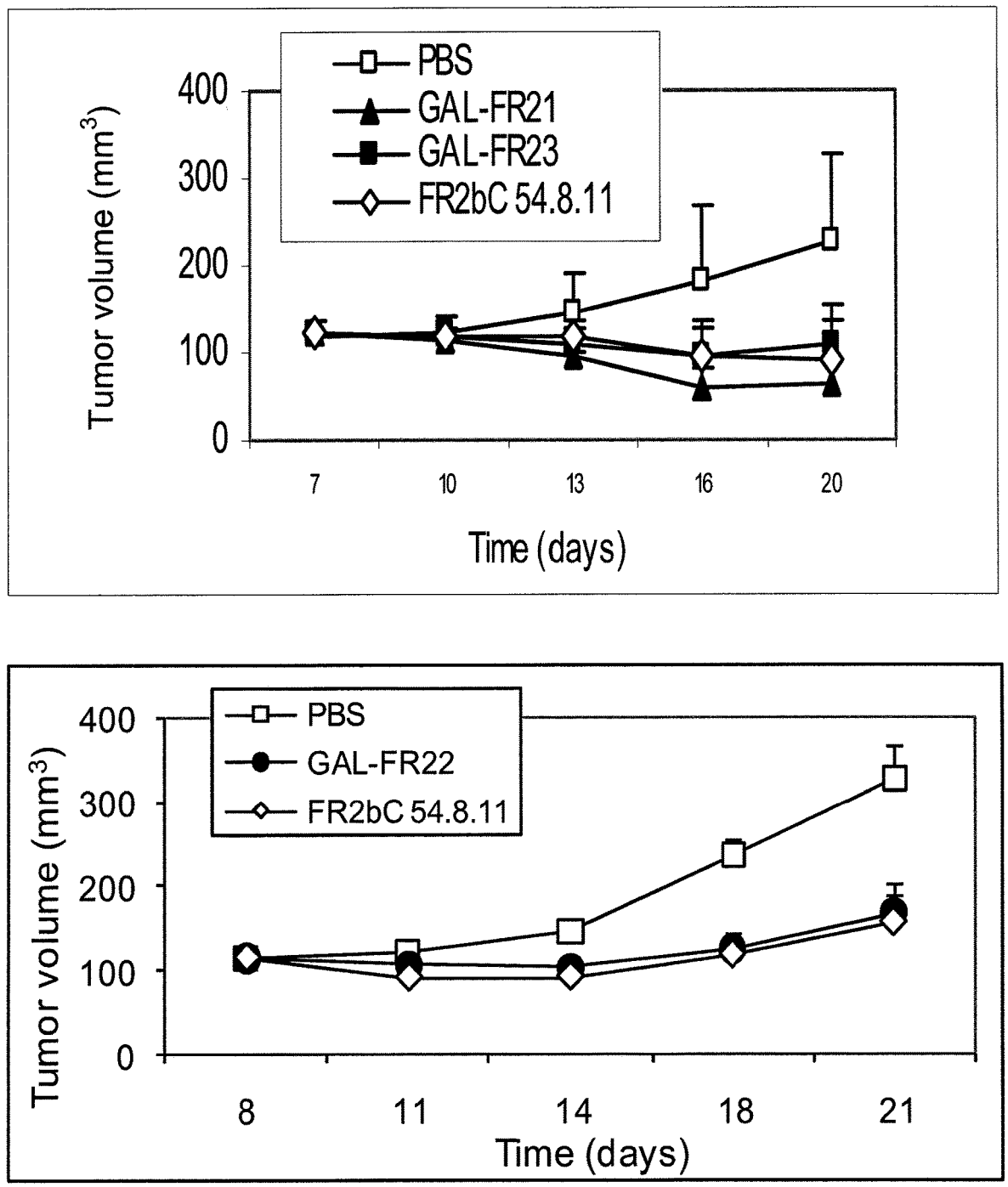
FIG. 9. Growth of SNU-16 human gastric tumor xenografts in mice treated with PBS alone, GAL-FR21, GAL-FR23 or FR2bC 54.8.11 (upper panel) or with PBS, GAL-FR22 or FR2bC 54.8.11 (lower panel). The mAbs were administered at 20 µg twice per week, about 5 mice per group.

FIGS. 9 and 10A show that in various experiments GAL-FR21, GAL-FR22 and GAL-FR23 administered at a dose level of 20 μg (1 mg/kg) twice per week all strongly inhibited the growth of SNU-16 gastric tumor xenografts, with GAL-FR21 being most potent and completely inhibiting growth of the xenograft. The mAb FR2bC 54.8.11 mentioned above that competes for binding with GAL-FR21 also inhibited xenograft growth. FIG. 10B shows that GAL-FR21 and GAL-FR22 administered at a dose level of 50 μg (2.5 mg/kg) twice per week also strongly inhibited growth of xenografts of the OCUM-2M human gastric tumor cell line (which is described in Yashiro et al., Jpn J Cancer Res 85:883, 1994). The ability of the mAbs to inhibit xenografts of KATO III or other FGFR2-expressing cell lines is shown similarly. The ability of the mAbs to inhibit tumor growth additively or synergistically with other anti-tumor agents as described above is demonstrated by treating groups of xenografted mice with the mAb alone, the other agent alone, and the mAb together with the other agent, and noting that treatment with both agents has a greater inhibitory effect than either agent alone.

Example 5: Binding of mAbs to FGFR2 from Other Species

To determine the ability of the mAbs to bind to FGFR2 from species other than human, ELISA assays were used. ELISA wells were coated with 2 μg/ml of goat anti-human IgG-Fc overnight at 4° C. After blocking with 2% BSA for 1 hr at RT, the wells were incubated with 0.2 μg/ml of FGFR2IIIb-Fc for 1 hr, where the FGFRIIIb in the fusion protein was either human, mouse, cynomolgus monkey or chimpanzee FGFRIIIb. The wells were then incubated with various concentrations of GAL-FR21 or GAL-FR22 mAb. The bound mAbs were detected by addition of HRP-conjugated goat anti-mouse IgG-Fc and then TMB substrate. FIG. 11 shows that GAL-FR21 binds to mouse FGFR2 almost as well (within 10-fold) as human FGFR2, while GAL-FR22 binds to mouse FGFR2 moderately well (within about 100-fold of human FGFR2). FIG. 12 shows that GAL-FR21 binds to cynomolgus monkey FGFR2 as well as (indistinguishably from) human FGFR2, while GAL-FR22 binds to cynomolgus monkey FGFR2 moderately well (within about 100-fold of human FGFR2). A similar experiment with chimpanzee FGFR2 gave the same results as with cynomolgus monkey FGFR2: GAL-FR21 bound to chimpanzee FGFR2 as well as (indistinguishably from) human FGFR2, while GAL-FR22 bound to chimpanzee FGFR2 moderately well (within about 100-fold of human FGFR2). Preferred mAbs of the invention, like GAL-FR21 and GAL-FR22, bind to al of mouse, monkey, chimpanzee and human FGFR2, and most preferably bind mouse FGFR2 within 2, 10, 100 or 1000 fold as well as human FGFR2, and/or bind monkey and/or chimpanzee FGFR2 within 2, 10 or 100-fold or indistinguishably from (within experimental variation) human FGFR2 (as measured, e.g., by $K_a$). Binding to FGFR2 from such other species makes testing of the mAbs in those animal species easier to conduct.

Example 6: Humanization of GAL-FR21 and GAL-FR22

Cloning of the light and heavy chain variable regions of the GAL-FR21 mAb, construction and expression of a chimeric mAb, and design, construction, expression and purification of a humanized GAL-FR21 mAb were all performed using standard methods of molecular biology, e.g. as described in US 20080019974 for the L2G7 mAb, which is herein incorporated by reference for all purposes. The amino acid sequences of the (mature) light and heavy chain variable (V) regions of GAL-FR21 are shown respectively in FIGS. 13A and 13B, top lines labeled GAL-FR21 (SEQ ID NOS:1 and 4). More specifically, to design a humanized GAL-FR21 mAb, the methods of Queen et al., U.S. Pat. Nos. 5,530,101 and 5,585,089 were generally followed. The human $V_K$ sequence CAG27369 (SEQ ID NO:3) and VH sequence AAB00780 (SEQ ID NO:6), as shown respectively in FIGS. 13A and 13B, bottom lines, were respectively chosen to serve as acceptor sequences for the GAL-FR21 VL and VH sequences because they have particularly high framework homology (i.e., sequence identity) to them. A computer-generated molecular model of the GAL-FR21 variable domain was used to locate the amino acids in the GAL-FR21 framework that are close enough to the CDRs to potentially interact with them. To design the humanized GAL-FR21 light and heavy chain variable regions, the CDRs from the mouse GAL-FR21 mAb were first conceptually grafted into the acceptor framework regions. At framework positions where the computer model suggested significant contact with the CDRs, which may be needed to maintain the CDR conformation, the amino acids from the mouse antibody were substituted for the human framework amino acids. For the humanized GAL-FR21 mAb designated HuGAL-FR21, this was done at residues 27, 28, 30 (within Chothia hypervariable loop H1) and 48 and 67 of the heavy chain and at no residues in the light chain, using Kabat numbering. The light and heavy chain V region sequences of HuGAL-FR21 are shown in FIGS. 13A and 13B respectively, middle lines labeled HuGAL-FR21 (SEQ ID NOS:2 and 5), where they are aligned against the respective GAL FR21 donor and human acceptor V regions—the CDRs (as defined by Kabat) are underlined and the substituted amino acids listed above are double-underlined.

The invention provides not only a humanized GAL-FR21 mAb, HuGAL-FR21, including the light and heavy chain V regions shown in FIG. 13, but also variant humanized mAbs whose light and heavy chain variable regions differ from the sequences of HuGAL-FR21 by a small number (e.g., typically no more than 1, 2, 3, 5 or 10) of replacements, deletions or insertions, usually in the framework but possibly in the CDRs. In particular, only a subset of the substitutions described above can be made in the acceptor frameworks, or additional substitution(s) can be made, e.g., the mouse GAL-FR21 VH amino acid 69L may replace the acceptor amino acid 69I, and/or the mouse amino acids may replace the respective amino acids in the humanized light chain at any of the Kabat-numbered positions 1, 3 and 60 and 63, which have some proximity to the CDRs. Indeed, many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered. One example of a CDR substitution is to substitute a residue in a CDR with the residue occupying the corresponding position of the human acceptor sequence used to supply variable region frameworks.

Most often the replacements made in the variant humanized GAL-FR21 sequences are conservative with respect to the replaced HuGAL-FR21 amino acids. Amino acids can be grouped as follows for determining conservative substitutions, i.e., substitutions within a group: Group I (hydrophobic sidechains): met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe.

Preferably, replacements in HuGAL-FR21 (whether or not conservative) have no substantial effect on the binding affinity or potency of the humanized mAb, that is, its ability to neutralize the biological activities of FGFR2 (e.g., the potency in some or all of the assays described herein of the variant humanized GAL-FR21 mAb is essentially the same, i.e., within experimental error, as that of HuGAL-FR21). Preferably the mature variant light and heavy chain V region sequences are at least 90%, more preferably at least 95%, and most preferably at least 98% identical to the respective HuGAL-FR21 mature light and heavy chain V regions. Alternatively, other human antibody variable regions with high sequence identity to those of GAL-FR21 are also suitable to provide the humanized antibody framework, especially kappa V regions from human subgroup I and heavy chain V regions from human subgroup I, or consensus sequences of these subgroups.

In other humanized antibodies, at least 1, 2, 3, 4, or all 5 of the positions of acceptor to donor substitutions mentioned in connection with the exemplified antibody (i.e., H27, H28, H30, H48, H67) are preferably occupied by the residue occupying the corresponding position of the mouse donor antibody heavy chain. If the heavy chain acceptor sequence is other than AAB00780 (SEQ ID NO:6), an acceptor to donor substitution may or may not be required for the specified occupancy of a particular variable framework region position depending on whether the residue occupying the specified position is already the same between the acceptor and donor.

Figure 14:
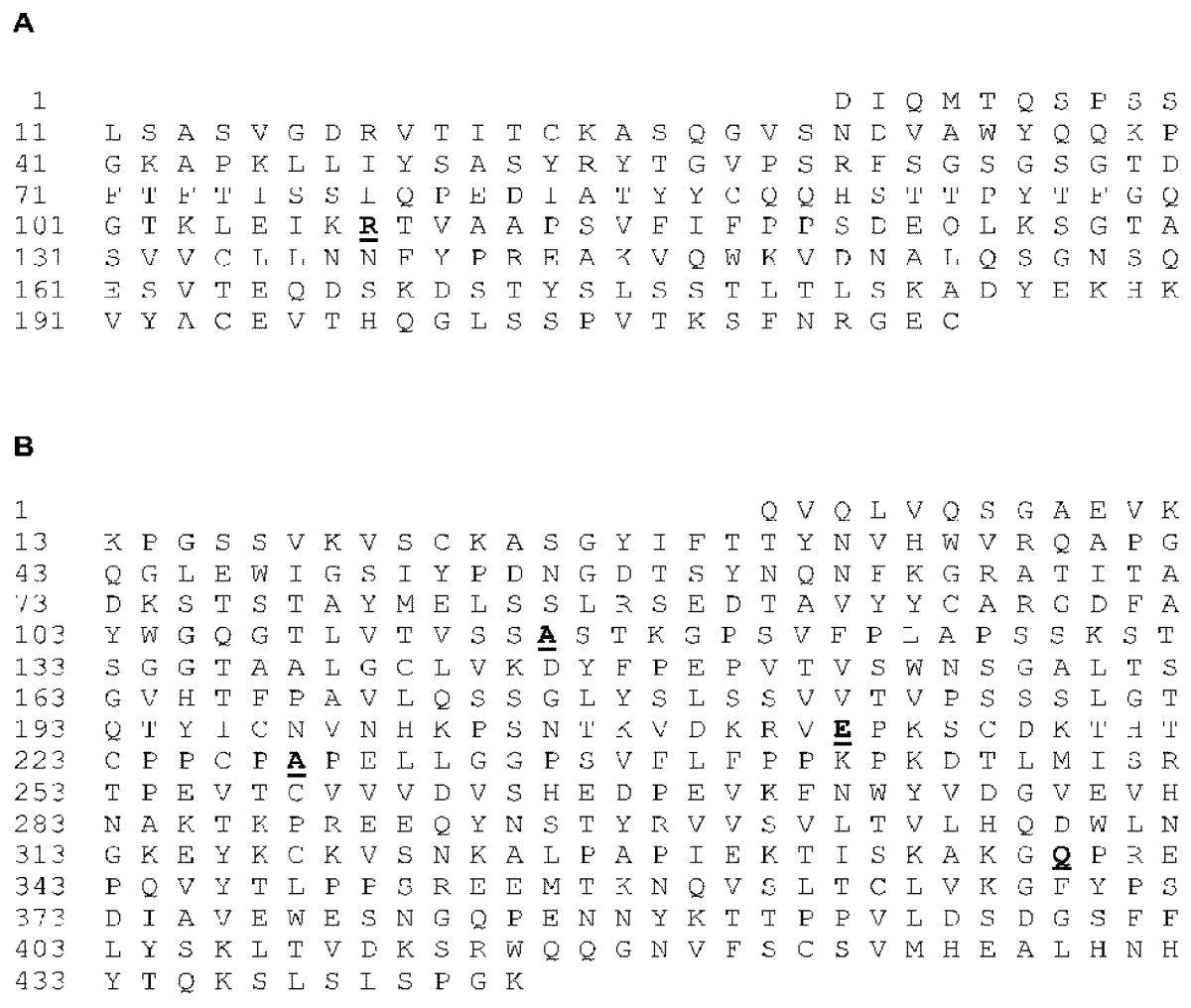

The exemplary mAb HuGAL-FR21 discussed here has human κ and γ1 constant regions, e.g., as presented in US 20080019974, and is therefore an IgG1. The complete sequences of the (mature) light and heavy chains of HuGAL-FR21 are shown in FIG. 14 (SEQ ID NOS:9 and 10). While these sequences are respectively of the Km(3) and G1m(3) allotypes, it is understood that IgG1 mAbs of any (IgG1, κ) allotype are encompassed by the designation HuGAL-FR21. It will also be understood that when HuGAL-FR21 is manufactured by conventional procedures, one to several amino acids at the amino or carboxy terminus of the light and/or heavy chain, such as the C-terminal lysine of the heavy chain, may be missing or derivatized in a proportion or all of the molecules, and such a composition will still be encompassed by the designation HuGAL-FR21 and considered a humanized GAL-FR21 mAb. Humanized mAbs of other isotypes (e.g., IgG2, IgG3 and IgG4) can be made by combining the HuGAL-FR21 variable regions with the appropriate human constant regions. Replacements can be made in the HuGAL-FR21 constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Specifically but without limitation, HuGAL-FR21 having mutations in the IgG constant region to a Gln at position 250 and/or a Leu at position 428 are embodiments of the present invention.

Figure 15:
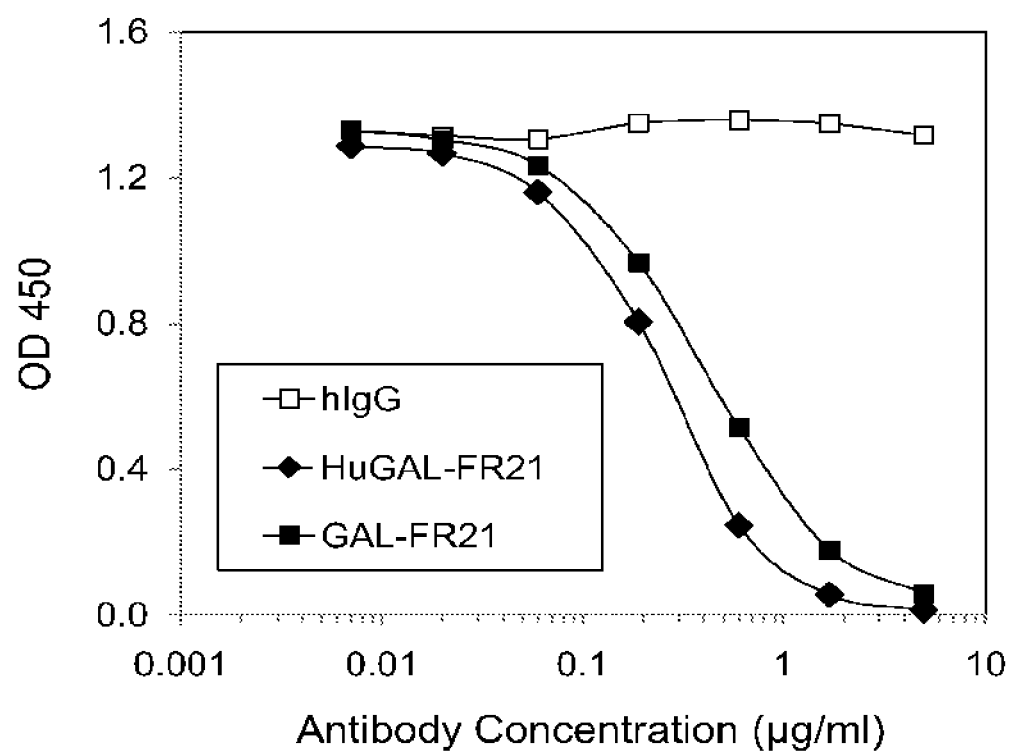
FIG. 15. Competitive binding of humanized HuGAL-FR21 and mouse GAL-FR21 mAbs and control human antibody hIgG, conducted as described in the specification.

To compare the binding affinity of HuGAL-FR21 with that of the mouse mAb GAL-FR21, a competitive binding experiment was performed using standard ELISA technology. Specifically, ELISA wells were coated with 2 µg/ml of goat anti-human IgG-Fc overnight at 4° C. After blocking with 2% BSA for 1 hr at RT, the wells were incubated with 0.5 µg/ml of FGFR2IIIb-Fc. The wells were then incubated with biotinylated GAL-FR21 mAb (0.05 µg/ml) in the presence of increasing concentrations of unlabeled GAL-FR21, HuGAL-FR21 or control human antibody hIgG. The level of biotinylated GAL-FR21 bound was determined by the addition of HRP-streptavidin and substrate. As shown in FIG. 15, HuGAL-FR21 and GAL-FR21 competed approximately equally well, with HuGAL-FR21 possibly slightly better, indicating that the binding affinity for FGFR2 of HuGAL-FR21 is at least as high as (mouse) GAL-FR21 mAb. From the concentration of HuGAL-FR21 required to inhibit binding of the labeled mAb by 50%, one may estimate that the binding affinity K of HuGAL-FR21 for FGFR2 is at least approximately $10^9$ $M^{-1}$. HuGAL-FR21 may also be tested in any of the biological assays for FGFR2 activity described herein. e.g., inhibition of binding of FGF2 or FGF7 to FGFR2, and will inhibit FGFR2 activity comparably to GAL-FR21.

A humanized GAL-FR22 mAb can be designed, constructed, produced and assayed in the same or similar way as HuGAL-FR21. The amino acid sequences of the (mature) light and heavy chain variable regions of GAL-FR22 are shown respectively in FIGS. 16A and 16B, lines labeled GAL-FR22. A humanized GAL-FR22 mAb has a humanized light chain comprising CDRs from the sequence in FIG. 16A and a humanized heavy chain comprising CDRs from the sequence of FIG. 16B. In some instances, the humanized GAL-FR22 mAb comprises the three light chain CDRs shown in FIG. 16A and the three heavy chain CDRs shown in FIG. 16B. Preferably, the humanized GAL-FR22 mAb has binding affinity for FGFR2 within 2 or 3 fold of the affinity of the mouse GAL-FR22 mAb, and most preferably has binding affinity indistinguishable or greater than the affinity of the GAL-FR22 mAb, as measured, e.g., by a competition ELISA as described for HuGAL-FR21 and GAL-FR21.

Although the invention has been described with reference to the presently preferred embodiments, it should be understood that various modifications can be made without departing from the invention. Unless otherwise apparent from the context any step, element, embodiment, feature or aspect of the invention can be used with any other. All publications, patents, patent applications, accession numbers and the like cited are herein incorporated by reference in their entirety for all purposes to the same extent as if each individual publication, patent, patent application or accession number was specifically and individually indicated to be incorporated by reference in its entirety for all purposes. If a nucleic acid or protein sequence associated with an accession number is changed, the version of the sequence associated with that accession number as of Nov. 7, 2008 is intended.

The hydridomas producing the monoclonal antibodies GAL-FR21, GAL-FR22, and GAL-FR23 have been deposited at the American Type Culture Collection, P.O. Box 1549 Manassas, Va. 20108, as respectively ATCC Numbers PTA-9586 on Nov. 6, 2008, PTA-9587 on Nov. 6, 2008 and PTA-9408 on Aug. 12, 2008, under the Budapest Treaty. These deposits will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

We claim:

1. A pharmaceutical composition comprising a monoclonal antibody (mAb) that binds human fibroblast growth factor receptor 2 isoform IIIb (FGFR2IIIb) comprising a light chain variable region comprising complementarity determining region (CDR)1, CDR2, and CDR3 respectively defined by residues 24-34, 50-56, and 89-97 of SEQ ID NO:1, and comprising a heavy chain variable region comprising CDR1, CDR2, and CDR3 respectively defined by residues 31-35, 50-66 and 99-103 of SEQ ID NO:4, and a pharmaceutically acceptable carrier.

2. The pharmaceutical composition of claim 1, wherein the light chain variable region is linked to a light chain constant region and the heavy chain variable region is linked to a heavy chain constant region.

3. The pharmaceutical composition of claim 1, wherein the mAb is a human IgG1 isotype.

4. The pharmaceutical composition of claim 1, wherein the light chain variable region comprises the sequence of SEQ ID NO:2 and the heavy chain variable region comprises the sequence of SEQ ID NO:5.

5. The pharmaceutical composition of claim 4, wherein the light chain variable region is linked to a light chain constant region and the heavy chain variable region is linked to a heavy chain constant region.

6. The pharmaceutical composition of claim 4, wherein the mAb is a human IgG1 isotype.

7. The pharmaceutical composition of claim 1, wherein the mAb comprises a light chain sequence comprising SEQ ID NO:9 and a heavy chain sequence comprising SEQ ID NO:10.

8. The pharmaceutical composition of claim 1, wherein the mAb comprises a light chain sequence comprising SEQ ID NO:9 and a heavy chain sequence comprising residues 1-432 of SEQ ID NO:10.

9. The pharmaceutical composition of claim 1, wherein the mAb is humanized.

10. A method of treating cancer in a human patient, comprising:
administering to the patient a therapeutically effective amount of a pharmaceutical composition of claim 1, wherein the cancer has an elevated level of FGFR2IIIb compared to normal tissues.

11. The method of claim 10, wherein the cancer is a solid tumor.

12. The method of claim 10, wherein the cancer is a gastric cancer.

13. The method of claim 10, further comprising administering a chemotherapy agent.

14. The method of claim 13, wherein the chemotherapy agent is a monoclonal antibody.

15. A method of treating cancer in a human patient comprising:
determining the level of expression of FGFR2IIIb in a tumor sample obtained from the patient; and
treating the patient with a therapeutically effective amount of the pharmaceutical composition of claim 1 if the level of FGFR2IIIb expression is elevated relative to expression in normal tissue.

16. The method of claim 15, wherein the cancer is a solid tumor.

17. The method of claim 15, wherein the cancer is gastric cancer.

18. The method of claim 15, wherein the level of expression of FGFR2IIIb is determined by immunohistochemistry (IHC).

* * * * *

SEQUENCE LISTING

```
<160> NUMBER OF SEQ ID NOS: 10

<210> SEQ ID NO 1
<211> LENGTH: 107
<212> TYPE: PRT
<213> ORGANISM: Mus sp.
<220> FEATURE:
<223> OTHER INFORMATION: light chain variable region of mAB GAL-FR21

<400> SEQUENCE: 1

Asn Ile Val Met Thr Gln Ser Pro Lys Ser Met Ser Met Ser Val Gly
1               5                   10                  15

Asp Arg Val Ser Ile Thr Cys Lys Ala Ser Gln Gly Val Ser Asn Asp
            20                  25                  30
```

Val Ala Trp Tyr Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Asn Val Gln Ala
65                  70                  75                  80

Glu Asp Leu Ala Val Tyr Tyr Cys Gln Gln His Ser Thr Thr Pro Tyr
                85                  90                  95

Thr Phe Gly Gly Gly Thr Lys Leu Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: light chain variable region of mAB HuGal-FR21

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Tyr
                85                  90                  95

Thr Phe Gly Gln Gly Thr Lys Leu Glu Ile Lys
            100                 105

<210> SEQ ID NO 3
<211> LENGTH: 107
<212> TYPE: PRT
<213> ORGANISM: Homo sapiens
<220> FEATURE:
<223> OTHER INFORMATION: human Vk sequence CAG27369

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Thr Phe Gly Gln Gly Thr Lys Leu Glu Ile Lys
            100                 105

-continued

<210> SEQ ID NO 4
<211> LENGTH: 114
<212> TYPE: PRT
<213> ORGANISM: Mus sp.
<220> FEATURE:
<223> OTHER INFORMATION: heavy chain variable region of mAB GAL-FR21

<400> SEQUENCE: 4

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Ile Phe Thr Thr Tyr
            20                  25                  30

Asn Val His Trp Val Lys Gln Thr Pro Gly Gln Gly Leu Glu Trp Ile
        35                  40                  45

Gly Ser Ile Tyr Pro Asp Asn Gly Asp Thr Ser Tyr Asn Gln Asn Phe
    50                  55                  60

Lys Gly Lys Ala Thr Leu Thr Ala Asp Lys Ser Ser Thr Ala Tyr
65                  70                  75                  80

Ile Gln Leu Ser Ser Leu Thr Ser Glu Asp Ser Ala Val Tyr Tyr Cys
                85                  90                  95

Ala Arg Gly Asp Phe Ala Tyr Trp Gly Gln Gly Thr Leu Val Thr Val
            100                 105                 110

Ser Val

<210> SEQ ID NO 5
<211> LENGTH: 114
<212> TYPE: PRT
<213> ORGANISM: Artificial Sequence
<220> FEATURE:
<223> OTHER INFORMATION: heavy chain variable region of mAB HuGal-FR21

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30

Asn Val His Trp Val Arg Gln Ala Pro Gly Gln Gly Leu Glu Trp Ile
        35                  40                  45

Gly Ser Ile Tyr Pro Asp Asn Gly Asp Thr Ser Tyr Asn Gln Asn Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Ala Tyr Trp Gly Gln Gly Thr Leu Val Thr Val
            100                 105                 110

Ser Ser

<210> SEQ ID NO 6
<211> LENGTH: 120
<212> TYPE: PRT
<213> ORGANISM: Homo sapiens
<220> FEATURE:
<223> OTHER INFORMATION: human VH sequence AAB00780

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr

```
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Ser Thr Val Thr Thr Gly Asp Phe Asp Tyr Trp Gly Gln
            100                 105                 110
Gly Thr Leu Val Thr Val Ser Ser
        115                 120

<210> SEQ ID NO 7
<211> LENGTH: 106
<212> TYPE: PRT
<213> ORGANISM: Mus Sp.
<220> FEATURE:
<223> OTHER INFORMATION: light chain variable region of mAB GAL-FR22

<400> SEQUENCE: 7

Asp Ile Gln Met Thr Gln Ser Pro Ser Ser Leu Ser Ala Ser Leu Gly
1               5                   10                  15
Gly Arg Val Thr Ile Thr Cys Lys Ala Ser Gln Asp Ile Lys Asn Tyr
            20                  25                  30
Ile Ala Trp Tyr Gln His Lys Pro Gly Lys Ser Pro Arg Leu Leu Ile
        35                  40                  45
His Tyr Thr Ser Thr Leu Gln Pro Gly Val Pro Ser Arg Phe Ser Gly
    50                  55                  60
Ser Gly Ser Gly Arg Asp Tyr Ser Phe Ser Ile Ser Asn Leu Glu Pro
65                  70                  75                  80
Glu Asp Ile Ala Thr Tyr Tyr Cys Leu Gln Tyr Asp Asp Leu Tyr Met
                85                  90                  95
Phe Gly Gly Gly Thr Lys Leu Asp Ile Lys
            100                 105

<210> SEQ ID NO 8
<211> LENGTH: 120
<212> TYPE: PRT
<213> ORGANISM: Mus sp.
<220> FEATURE:
<223> OTHER INFORMATION: heavy chain variable region of mAB GAL-FR22

<400> SEQUENCE: 8

Gln Val Gln Leu Lys Gln Ser Gly Pro Gly Leu Val Gln Pro Ser Gln
1               5                   10                  15
Ser Leu Ser Ile Thr Cys Thr Val Ser Gly Phe Ser Leu Thr Ser Phe
            20                  25                  30
Gly Val His Trp Val Arg Gln Ser Pro Gly Lys Gly Leu Glu Trp Leu
        35                  40                  45
Gly Val Ile Trp Ser Gly Gly Ser Thr Asp Tyr Asn Ala Asp Phe Arg
    50                  55                  60
Ser Arg Leu Ser Ile Ser Lys Asp Asn Ser Lys Ser Gln Ile Phe Phe
65                  70                  75                  80
Lys Met Asn Ser Leu Gln Pro Asp Asp Thr Ala Ile Tyr Tyr Cys Ala
                85                  90                  95
```

```
Asn Phe Tyr Tyr Gly Tyr Asp Asp Tyr Val Met Asp Tyr Trp Gly Gln
                100                 105                 110

Gly Thr Ser Val Thr Val Ser Ser
        115                 120

<210> SEQ ID NO 9
<211> LENGTH: 214
<212> TYPE: PRT
<213> ORGANISM: Artificial Sequence
<220> FEATURE:
<223> OTHER INFORMATION: complete mature light chain sequence of mAB
      HuGAL-FR21

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Ser Asn Asp
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Ser Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 444
<212> TYPE: PRT
<213> ORGANISM: Artificial Sequence
<220> FEATURE:
<223> OTHER INFORMATION: complete mature heavy chain sequence of mAB
      HuGAL-FR21

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Thr Tyr
            20                  25                  30

Asn Val His Trp Val Arg Gln Ala Pro Gly Gln Gly Leu Glu Trp Ile
        35                  40                  45
```

```
Gly Ser Ile Tyr Pro Asp Asn Gly Asp Thr Ser Tyr Asn Gln Asn Phe
     50                  55                  60

Lys Gly Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Phe Ala Tyr Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Arg Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```